(12) United States Patent  (10) Patent No.: US 12,298,300 B2
Lindsay et al.  (45) Date of Patent: May 13, 2025

(54) SINGLE-MOLECULE ELECTRONIC SEQUENCE DETECTOR AND METHODS OF USE

(71) Applicants: ARIZONA BOARD OF REGENTS ON BEHALF OF ARIZONA STATE UNIVERSITY, Scottsdale, AZ (US); RECOGNITION ANALYTIX INC., Phoenix, AZ (US)

(72) Inventors: Stuart Lindsay, Scottsdale, AZ (US); Karen Anderson, Scottsdale, AZ (US); Mark Knappenberger, Scottsdale, AZ (US); Sepideh Afsari Mamaghani, Scottsdale, AZ (US); Jacob L. Swett, Tempe, AZ (US)

(73) Assignees: Arizona Board of Regents on behalf of Arizona State University, Scottsdale, AZ (US); Recognition Analytix, Inc., Phoenix, AZ (US)

( * ) Notice: Subject to any disclaimer, the term of this patent is extended or adjusted under 35 U.S.C. 154(b) by 1063 days.

(21) Appl. No.: 17/232,631

(22) Filed: Apr. 16, 2021

(65) Prior Publication Data
US 2021/0325379 A1  Oct. 21, 2021

Related U.S. Application Data

(60) Provisional application No. 63/011,799, filed on Apr. 17, 2020.

(51) Int. Cl.
G01N 33/53 (2006.01)
C12N 9/22 (2006.01)
(Continued)

(52) U.S. Cl.
CPC .......... *G01N 33/5308* (2013.01); *C12N 9/22* (2013.01); *C12N 15/11* (2013.01); *G01N 27/021* (2013.01);
(Continued)

(58) Field of Classification Search
None
See application file for complete search history.

(56) References Cited

U.S. PATENT DOCUMENTS 5,198,543 A 3/1993 Blanco
6,824,974 B2 11/2004 Pisharody et al.
(Continued)

FOREIGN PATENT DOCUMENTS

CN 104359946 2/2015
JP 2016188794 A 11/2016
(Continued)

OTHER PUBLICATIONS

Hajian et al., Detection of unamplified target genes via CRISPR-Cas9 immobilized on a graphene field-effect transistor. Nat Biomed Eng. Jun. 2019;3(6):427-437.
(Continued)

*Primary Examiner* — J. Christopher Ball
(74) *Attorney, Agent, or Firm* — Casimir Jones, S.C.; Peter J. Schlueter

(57) ABSTRACT

The present disclosure provides devices, systems, and methods related to single molecule detection. In particular, the present disclosure provides devices and methods for sequence-specific detection of a nucleic acid target using current fluctuations as a readout for protein binding to the nucleic acid target. As described herein, certain aspects of the bioelectronic devices and method can be used to detect
(Continued)

and identify any nucleic acid target for the purpose of diagnosis and/or treatment.

27 Claims, 8 Drawing Sheets

Specification includes a Sequence Listing.

(51) Int. Cl.
*C12N 15/11* (2006.01)
*G01N 27/02* (2006.01)
(52) U.S. Cl.
CPC ...... *C12N 2310/20* (2017.05); *C12N 2800/80* (2013.01)

(56) References Cited

U.S. PATENT DOCUMENTS

| | | |
|---|---|---|
| 7,632,671 B2 | 12/2009 | Tong |
| 8,628,649 B2 | 1/2014 | Lindsay et al. |
| 8,961,757 B2 | 2/2015 | Nuckolls et al. |
| 8,968,540 B2 | 3/2015 | Reinhart et al. |
| 9,140,682 B2 | 9/2015 | Lindsay et al. |
| 9,274,430 B2 | 3/2016 | Gyarfas et al. |
| 9,376,713 B2 | 6/2016 | Bashir et al. |
| 9,593,372 B2 | 3/2017 | Lindsay et al. |
| 9,938,586 B2 | 4/2018 | Liang et al. |
| 10,047,392 B2 | 8/2018 | Ivankin et al. |
| 10,051,722 B2 | 12/2018 | Jin et al. |
| 10,227,694 B2 | 3/2019 | Jin et al. |
| 10,378,103 B2 | 8/2019 | Jin et al. |
| 10,379,102 B2 | 8/2019 | Lindsay et al. |
| 10,422,787 B2 | 9/2019 | Lindsay et al. |
| 10,508,296 B2 | 12/2019 | Merriman et al. |
| 10,526,696 B2 | 1/2020 | Jin et al. |
| 10,584,410 B2 | 3/2020 | Jin et al. |
| 10,597,767 B2 | 3/2020 | Merriman et al. |
| 10,648,941 B2 | 5/2020 | Merriman et al. |
| 10,712,334 B2 | 7/2020 | Choi et al. |
| 10,737,263 B2 | 8/2020 | Choi et al. |
| 10,913,966 B2 | 2/2021 | Merriman et al. |
| 2003/0124572 A1 | 7/2003 | Umek et al. |
| 2004/0146863 A1 | 7/2004 | Pisharody et al. |
| 2004/0249124 A1 | 12/2004 | Caruso et al. |
| 2005/0285275 A1 | 12/2005 | Son et al. |
| 2009/0215156 A1 | 8/2009 | Chung et al. |
| 2009/0226899 A1 | 9/2009 | Chen |
| 2010/0084276 A1 | 4/2010 | Lindsay |
| 2010/0184062 A1 | 7/2010 | Steinmuller-Nethl et al. |
| 2010/0206731 A1 | 8/2010 | Lau et al. |
| 2010/0285514 A1 | 11/2010 | Claussen et al. |
| 2011/0098218 A1 | 4/2011 | Han et al. |
| 2011/0312529 A1 | 12/2011 | He et al. |
| 2012/0228386 A1 | 9/2012 | Wu et al. |
| 2013/0302901 A1 | 11/2013 | Lindsay et al. |
| 2014/0141525 A1 | 5/2014 | Albert et al. |
| 2015/0010935 A1 | 1/2015 | Lindsay et al. |
| 2015/0017655 A1 | 1/2015 | Huang et al. |
| 2015/0086994 A1 | 3/2015 | Williams et al. |
| 2015/0142327 A1 | 5/2015 | Ashcroft et al. |
| 2015/0144506 A1 | 5/2015 | Lindsay et al. |
| 2015/0285818 A1 | 10/2015 | Banala et al. |
| 2015/0362459 A1 | 12/2015 | Chung et al. |
| 2016/0018384 A1 | 1/2016 | Lindsay et al. |
| 2016/0025702 A1 | 1/2016 | Lindsay et al. |
| 2016/0083789 A1 | 3/2016 | Turner et al. |
| 2016/0097759 A1 | 4/2016 | Lindsay et al. |
| 2016/0108002 A1 | 4/2016 | Zhang et al. |
| 2016/0146828 A1 | 5/2016 | Lindsay et al. |
| 2016/0177383 A1 | 6/2016 | Ashcroft et al. |
| 2016/0194698 A1 | 7/2016 | Lindsay |
| 2016/0258925 A1 | 9/2016 | Gyarfas et al. |
| 2016/0280723 A1 | 9/2016 | Zhang et al. |
| 2016/0282295 A1 | 9/2016 | Wang et al. |
| 2016/0319343 A1 | 11/2016 | Korlach et al. |
| 2017/0003245 A1 | 1/2017 | Lindsay et al. |
| 2017/0016852 A1 | 1/2017 | Lindsay et al. |
| 2017/0037462 A1 | 2/2017 | Turner et al. |
| 2017/0038333 A1 | 2/2017 | Turner et al. |
| 2017/0038369 A1 | 2/2017 | Lindsay et al. |
| 2017/0044605 A1 | 2/2017 | Merriman et al. |
| 2017/0067902 A1 | 3/2017 | Zhang et al. |
| 2017/0137389 A1 | 5/2017 | Zhang et al. |
| 2017/0168039 A1 | 6/2017 | Lindsay et al. |
| 2017/0276678 A1 | 9/2017 | Ervin |
| 2018/0031549 A1 | 2/2018 | Chen et al. |
| 2018/0073071 A1 | 3/2018 | Ju et al. |
| 2018/0095081 A1 | 4/2018 | Albert et al. |
| 2018/0120286 A1 | 5/2018 | Lindsay et al. |
| 2018/0155773 A1 | 6/2018 | Gunderson et al. |
| 2018/0180567 A1 | 6/2018 | Li et al. |
| 2018/0305727 A1 | 10/2018 | Merriman et al. |
| 2018/0340220 A1 | 11/2018 | Merriman et al. |
| 2019/0004003 A1 | 1/2019 | Merriman et al. |
| 2019/0041355 A1 | 2/2019 | Merriman et al. |
| 2019/0094175 A1 | 3/2019 | Merriman et al. |
| 2019/0112643 A1 | 4/2019 | Aran et al. |
| 2019/0234902 A1 | 8/2019 | Lima, Jr. et al. |
| 2019/0309008 A1 | 10/2019 | Ju et al. |
| 2019/0317040 A1 | 10/2019 | Lindsay et al. |
| 2019/0330695 A1 | 10/2019 | Guo et al. |
| 2019/0376135 A1 | 12/2019 | Mandell et al. |
| 2020/0157595 A1 | 5/2020 | Merriman et al. |
| 2021/0114025 A1 | 4/2021 | De Freitas Dias et al. |
| 2021/0208127 A1 | 7/2021 | Lindsay et al. |
| 2022/0252542 A1 | 8/2022 | Merriman et al. |

FOREIGN PATENT DOCUMENTS

| | | |
|---|---|---|
| WO | WO 2013/038272 | 3/2013 |
| WO | WO 2013/154999 | 10/2013 |
| WO | WO 2014/074727 | 5/2014 |
| WO | WO 2015/130781 | 9/2015 |
| WO | WO 2015/131073 | 9/2015 |
| WO | WO 2015/161119 | 10/2015 |
| WO | WO 2015/170784 | 11/2015 |
| WO | WO 2016/100635 A1 | 6/2016 |
| WO | WO 2016/161402 | 10/2016 |
| WO | WO 2016/210386 | 12/2016 |
| WO | WO 2017/084998 | 5/2017 |
| WO | WO 2017/123416 | 7/2017 |
| WO | WO 2017/189930 | 11/2017 |
| WO | WO 2018/026855 | 2/2018 |
| WO | WO 2018/132457 | 7/2018 |
| WO | WO 2018/200687 | 11/2018 |
| WO | WO 2018/208505 | 11/2018 |
| WO | WO 2019/046589 | 3/2019 |
| WO | WO 2019/086305 | 5/2019 |
| WO | WO 2019/211622 | 11/2019 |
| WO | WO 2019/217600 | 11/2019 |
| WO | WO 2019/222527 A1 | 11/2019 |
| WO | WO 2020/160300 | 8/2020 |
| WO | WO 2020/243207 | 12/2020 |
| WO | WO 2020/257654 | 12/2020 |
| WO | WO 2021/163275 | 8/2021 |
| WO | WO 2021/173681 | 9/2021 |
| WO | WO 2021/222791 | 11/2021 |

OTHER PUBLICATIONS

International Search Report and Written Opinion for PCT/US21/27650. Mailed Aug. 25, 2021. 9 pages.

Ackerman et al., Massively multiplexed nucleic acid detection with Cas13. Nature. Jun. 2020;582(7811):277-282.

Altschul et al., Basic local alignment search tool. J Mol Biol. Oct. 5, 1990;215(3):403-10.

Altschul et al., Gapped BLAST and PSI-BLAST: a new generation of protein database search programs. Nucleic Acids Res. Sep. 1, 1997;25(17):3389-402.

Ausubel et al. Current Protocols in Molecular Biology, John Wiley & Sons, New York, 1998.

(56) References Cited

OTHER PUBLICATIONS

Gonnet et al., Exhaustive matching of the entire protein sequence database. Science. Jun. 5, 1992;256(5062):1443-5.
Kyte et al., A simple method for displaying the hydropathic character of a protein. J Mol Biol. May 5, 1982;157(1):105-32.
Li et al., CRISPR-SE: a brute force search engine for CRISPR design. NAR Genom Bioinform. Feb. 23, 2021;3(1):lqab013.
Marakova et al., An updated evolutionary classification of CRISPR-Cas systems. Nat Rev Microbiol. Nov. 2015;13(11):722-36.
Metsky et al., Diagnostic design with machine learning model-based optimization. bioRxiv 2020.11.28.401877: 95 pages.
Mullegama et al., Nucleic Acid Extraction from Human Biological Samples. Methods Mol Biol 2019;1897:359-383.
Pearson. Using the FASTA program to search protein and DNA sequence databases. Methods Mol Biol. 1994;24:307-31.
Staals et al., RNA targeting by the type III-A CRISPR-Cas Csm complex of Thermus thermophilus. Mol Cell. Nov. 20, 2014;56(4):518-30.
Zhang et al., Engineering an Enzyme for Direct Electrical Monitoring of Activity. ACS Nano. Feb. 25, 2020;14(2):1360-1368.
Adhikari et al., Conductivity of individual Geobacter pili. RSC Advances, 2016. 6: p. 8354-8357.
Alloway et al., Interface Dipoles Arising from Self-Assembled Monolayers on Gold: UV-Photoemission Studies of Alkanethiols and Partially Fluorinated Alkanethiols. J. Phys. Chem. B 2003, 107:11690-11699.
Amdursky et al., Electronic transport via proteins. Adv Mater. Nov. 12, 2014;26(42):7142-61.
Amdursky et al., Solid-state electron transport via cytochrome c depends on electronic coupling to electrodes and across the protein. PNAS, Apr. 15, 2014, vol. 111, No. 15, pp. 5556-5561.
Anzai et al., Avidin-biotin complexation for enzyme sensor Applications, Trends in Analytical Chemistry, 1994, 13(5): 205-210.
Artes et al., Transistor-like Behavior of Single Metalloprotein Junctions. Nano Lett.,2012, 12(6), pp. 2679-2684 (publication date (Web): Oct. 5, 2011).
Aubert et al., Intraprotein radical transfer during photoactivation of DNA photolyase. Nature. Jun. 1, 2000; 405(6786):586-90.
Barhoumi et al., Urease immobilization on biotinylated polypyrrole coated ChemFEC devices for urea biosensor development, IRBM, Apr. 1, 2008, 29(2-3):192-201.
Bostick et al., Protein bioelectronics: a review of what we do and do not know. Rep Prog Phys. Feb. 2018;81(2):026601. 58 pages.
Carter et al., Functional protein materials: beyond elastomeric and structural proteins, Polym. Chem. 2019, 10:2952-2959.
Castellarnau et al., Integrated microanalytical system based on electrochemical detection and cell positioning, Materials Science and Engineering, 2006, 26: 405-410.
Chang et al., Chemical recognition and binding kinetics in a functionalized tunnel junction. Nanotechnology. Jun. 15, 2012;23(23):235101. 28 pages.
Chen et al., DNA sequencing using electrical conductance measurements of a DNA polymerase, Nature Nanotechnology, May 5, 2013, pp. 1-7; https://doi.org/10.1038/nnano.2013.71. 7 pages.
Chichil et al., Linkers in the structural biology of protein-protein interactions. Protein Sci. Feb. 2013;22(2):153-67.
Chin et al., Addition of p-Azido-I-phenylalanine to the Genetic Code of *Escherichia coli*. J. Am. Chem. Soc. 2002. 124,31, 9026-9027.
Choi et al. Site-specific inhibition of integrin alpha v beta 3-vitronectin association by a serasp-val sequence through an Arg-Gly-Asp-binding site of the integrin, Proteomics, vol. 10, Issue 1, No. 1 Jan. 2010, pp. 72-80 (First published Oct. 30, 2009).
Choi et al., Single-Molecule Lysozyme Dynamics Monitored by an Electronic Circuit, Science (2012) 335:319-324.
Cui et al., Reproducible measurement of single-molecule conductivity. Science. Oct. 19, 2001;294(5542):571-4.
Cui et al., Layer-by-layer 1 assembly of multilayer filme composed of avidin and biotin-labeled antibody for immunosensing, Biosensors And Bioelectronics, Jan. 1, 2003, 18(1): 59-67.

Dellafiore et al., Modified Nucleoside Triphosphates for In-vitro Selection Techniques. Front Chem. May 4, 2016;4:18.
Dissertation by Joshua Sadar, Top-Down and Bottom-Up Strategies to Prepare Nanogap Sensors for Controlling and Characterizing Single Biomolecules, Jul. 2019, 160 pages.
Duffy et al., Modified nucleic acids: replication, evolution, and next-generation therapeutics. BMC Biology, Sep. 2, 2020. 18:112. 14 pages.
Fairhead et al., Plug-and-play pairing via defined divalent streptavidins. J Mol Biol. Jan. 9, 2014;426(1):199-214.
Fujino et al., Chimeric RNA Oligonucleotides Incorporating Triazole-Linked Trinucleotides: Synthesis and Function as mRNA in Cell-Free Translation Reactions. J Org Chem. Oct. 7, 2016;81(19):8967-8976.
Fulton et al., Purification of monoclonal antibody against Ebola GP1 protein expressed in Nicotiana benthamiana. J Chromatogr A. Apr. 10, 2015; 1389:128-32.
Garg et al., Interface Electrostatics Dictates the Electron Transport via Bioelectronic Junctions. ACS Appl Mater Interfaces. Dec. 5, 2018;10(48):41599-41607.
Giese et al., Direct observation of hole transfer through DNA by hopping between adenine bases and by tunnelling. Nature. Jul. 19, 2001;412(6844):318-20.
Giese et al., Long distance charge transport through DNA: quantification and extension of the hopping model. Chemphyschem. Dec. 5, 2000;1(4):195-8.
Guo et al., Tuning electronic transport via hepta-alanine peptides junction by tryptophan doping. Proc Natl Acad Sci U S A. Sep. 27, 2016;113(39):10785-90.
Harriman. Further comments on the redox potentials of tryptophan and tyrosine. Journal of Physical Chemistry 1987. 91:6102-6104.
Hays et al., Development of capacitance based immunosensors on mixed self-assembled monolayers. Sensors and Actuators B: Chemical, Apr. 26, 2006, 114(2):1064-1070.
Hohl et al. Engineering a Polyspecific Pyrrolysyl-tRNA Synthetase by a High Throughput FACS Screen. Sci Rep. Aug. 19, 2019;9(1):11971.
Hozel et al., Trapping Single Molecules by Dielectrophoresis, Physical Review Letters, 2005, 128102-1-4.
Ihalainene et al., Application of paper-supported printed gold eletrodes for impedimetric immunosensor development, Biosensors 2013, 3:1-17.
Jeffrey, An Introduction to Hydrogen Bonding. Oxford University Press New York. 1997. TOC only. 6 pages.
Kluenker et al., Monitoring Thiol-Ligand exchange on Au nanoparticle surfaces. Langmuir. Jan. 30, 2018;34(4):1700-1710.
Kotlowski, Fine discrimination of volatile compounds by graphene-immobilized odorant-binding proteins, Sensors and Actuatores B: Chemical 2018 (256): 564-72.
Krishnan et al., Long-Range Conductivity in Proteins Mediated by Aromatic Residues, ACS Phys. Chem Au 2023, 3:444-455.
Lagunas et al., Long distance electron transfer through the aqueous solution between redox partner proteins. Nat Commun. Dec. 4, 2018;9(1):5157.
Lai et al., Monoclonal antibody produced in plants efficiently treats West Nile virus infection in mice. Proc Natl Acad Sci U S A. Feb. 9, 2010;107(6):2419-24.
Lai et al., Robust production of virus-like particles and monoclonal antibodies with geminiviral replicon vectors in lettuce. Plant Biotechnol J. Jan. 2012;10(1):95-104.
Leary et al., Unambiguous one-molecule conductance measurements under ambient conditions. Nano Lett. Jun. 8, 2011;11(6):2236-41.
Li et al., Synthesis and Photovoltaic effect on electron-withdrawing units for low band gap conjugated polymers bearing bi(thienylenevinylene) side chains. Polymers. 2019, vol. 11 iss 9 pp. 1-13.
Lindsay et al., Recognition tunneling, Nanotechnology 2010, 21:262001, 12 pp.
Lindsay. Ubiquitous Electron Transport in Non-Electron Transfer Proteins. Life (Basel). May 20, 2020;10(5):72. 13 pages.
Liu et al., Vertical T cellimmunodomincance and epitope entropy determine HIV-1 escape. J Clin Invest. Jan. 2013;123(1):380-93.

(56) References Cited

OTHER PUBLICATIONS

Maalouf R. et al., Label-Free Detection of Bacteria by Electrochemical Impedance Spectroscopy: Comparison to Surface Plasmon Resonance. Anal. Chem, May 25, 2007, vol. 79, No. 13, pp. 4879-4886.

Main et al., Design of stable alpha-helical arrays from an idealized TPR motif. Structure. May 2003;11(5):497-508.

Malvankar et al., Tunable metallic-like conductivity in microbial nanowire networks. Nat Nanotechnol. Aug. 7, 2011;6(9):573-9.

Mckenzie et al., Recent progress in non-native nucleic acid modifications. Chem Soc Rev. Apr. 26, 2021;50(8):5126-5164.

Mejias et al., Controlled nanometric fibers of self-assembled designed protein scaffolds. Nanoscale. Oct. 7, 2014;6(19):10982-8.

Nitzan. Chemical dynamics in condensed phases. Oxford University Press., Oxford. 2006. TOC only. 13 pages.

Odella et al., Controlling Proton-Coupled Electron Transfer in Bioinspired Artificial Photosynthetic Relays. J Am Chem Soc. Nov. 14, 2018;140(45):15450-15460.

Olsen et al., Electronic Measurements of Single-Molecule Processing by DNA Polymerase I (Klenow Fragment), Journal of the American Chemical Society (Apr. 30, 2013); pp. 1-12; DOI: 10.1021/ja311603r.

Ouerghi et al., Impedimetric immunosensor using avidin-biotin for antibody immobilization, Bioelectrochemistry, May 15, 2002, 56(1-2): 131-133.

Pang et al. Fixed-Gap Tunnel Junction for Reading DNA Nucleotides, ACS Nano, 2014, 8(12), pp. 11994-12003 (Publication Date (Web): Nov. 7, 2014).

Prodromidis et al., Impedimetric immunosensors—A review, Electrochimica Acta, May 30, 2010, 55(14): 4227-4233.

Quast et al., Cotranslational incorporation of non-standard amino acids using cell-free protein synthesis. FEBS Lett. Jul. 8, 2015;589(15):1703-12.

Ruiz et al., Bioengineering a Single-Protein Junction. J Am Chem Soc. Nov. 1, 2017;139(43):15337-15346.

Sambrook et al., Molecular Cloning: A Laboratory Manual, 3d ed., Cold Spring Harbor Press, 2001. TOC only. 23 pages.

Sano et al., Cooperative biotin binding by streptavidin. Electrophoretic behavior and subunit association of streptavidin in the presence of 6 M urea. J Biol Chem. Feb. 25, 1990;265(6):3369-73.

Seifert, Characterization of Streptavidin Binding to Biotinylated, Binary Self-Assembled Thio Monolayers-Influence of Component Ratio and Solvent, Langmuir, 2010, 26(9): 6386-93.

Sek et al., Conductance of alpha-helical peptides trapped within molecular junctions. J Phys Chem B. Oct. 5, 2006;110(39):19671-7.

Sela-Culang et al., The strutural basis of antibody-antigen recognition, Frontiers in Immunology, 2013, vol. 4, 13 pages.

Sequences of amino acids as found on the world wide web at bmrb.wisc.edu/referenc/choufas. 4 pages.

Shimura & Yoshida, Heterogeneous photocatalytic hydrogen production from water and biomass derivatives Energy Environmental Science 2011, 4: 2467.

Smith. The hydrophilic nature of a clean gold surface. J. Colloid Interface Science 1980. 75:51-55.

Tripkovic et al., Standard hydrogen electrode and potential of zero charge in density functional calculations. Phys. Rev. B 2011. 84:115452.

Tuchband et al., Insulated gold scanning tunneling microscopy probes for recognition tunneling in an aqueous environment. Rev Sci Instrum. Jan. 2012;83(1):015102.

Uygun et al., CRISPR-dCAS9 powered impedimetric biosensor for label-free detection of circulating tumor DNAs, Analytica Chimica Acta 2020, 1121:35-41.

Vaish et al., A novel, modification-dependent ATP-binding aptamer selected from an RNA library incorporating a cationic functionality. Biochemistry. Jul. 29, 2003;42(29):8842-51.

Varga et al., Binding of a Mouse Monoclonal IgE (anti-DNP) antibody to radio-derivatized polystyrene-DNP complexes, The FASEB Journal, Federation of American Societies for Experimental Biology, Jun. 1, 1990, 4(9): 2678-2683.

Vattay et al., Quantum Criticality at the Origin of Life. Journal of Physics: Conference Series 2015. 626: p. 012023. 11 pages.

Willner et al., Mediated electron transfer in glutathione reductase organized in self-assembled monolayers on Au electrodes. J. Am. Chem. Soc., 1992. 114: p. 10965-10966.

Xiao et al., Conductance titration of single-peptide molecules. J Am Chem Soc. May 5, 2004;126(17):5370-1.

Yang et al., Plant-produced Zika virus envelope protein elicits neutralizing immune responses that correlate with protective immunity against Zika virus in mice. Plant Biotechnol J. Feb. 2018;16(2):572-580.

Yoon, Hidden Markov Models and their Applications in Biological Sequence Analysis, Current Genomics, 2009, 10:402-415.

Zhang et al., Electronic Transport in Molecular Wires of Precisely Controlled Length Built from Modular Proteins, ACS Nano 2022, 16(1): 1671-1680.

Zhang et al., Electronic Conductance Resonance in Non-Redox-Active Proteins. J Am Chem Soc. Apr. 1, 2020;142(13):6432-6438.

Zhang et al., Electronic Decay Length in a Protein Molecule. Nano Lett. Jun. 12, 2019;19(6):4017-4022.

Zhang et al., Observation of Giant Conductance Fluctuations in a Protein. Nano Futures. 2017;1(3):035002. 25 pages.

Zhang et al., Role of contacts in long-range protein conductance. Proc Natl Acad Sci U S A. Mar. 26, 2019;116(13):5886-5891.

Zwolak et al. Electronic Signature of DNA Nucleotides via Transverse Transport, NanoLett., 2005, 5(3), pp. 421-424 (Publication Date (Web): Feb. 12, 2005).

European Search Report and Written Opinion dated Apr. 4, 2024, European Application No. 21789574.7, 8 pages.

Bayer et al., 3-(N-Maleimido-propionyl) Biocytin: A Versatile Thiol-Specific Biotinylating Reagent, Analytical Biochemistry, 1985, 149: 529-536.

Gerrits et al., Cell-Free Synthesis of Defined Protein Conjugates by Site directed Cotranslational Labeling, NCBI Bookshelf. Jan. 1, 2013, Retrieved from the Internet: URL:https://ww.ncbi.nlm.nih.gov/books/NBK6497.

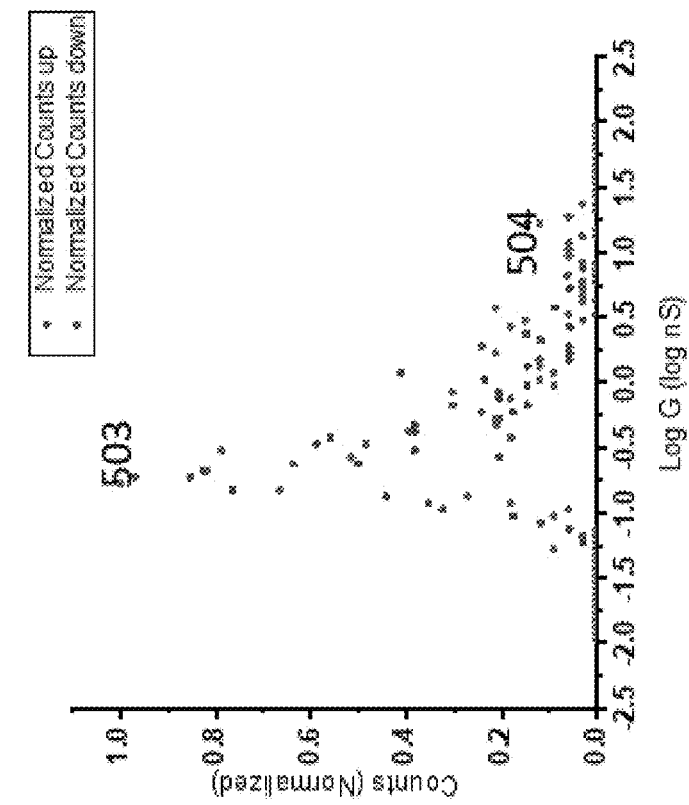
FIG. 5A
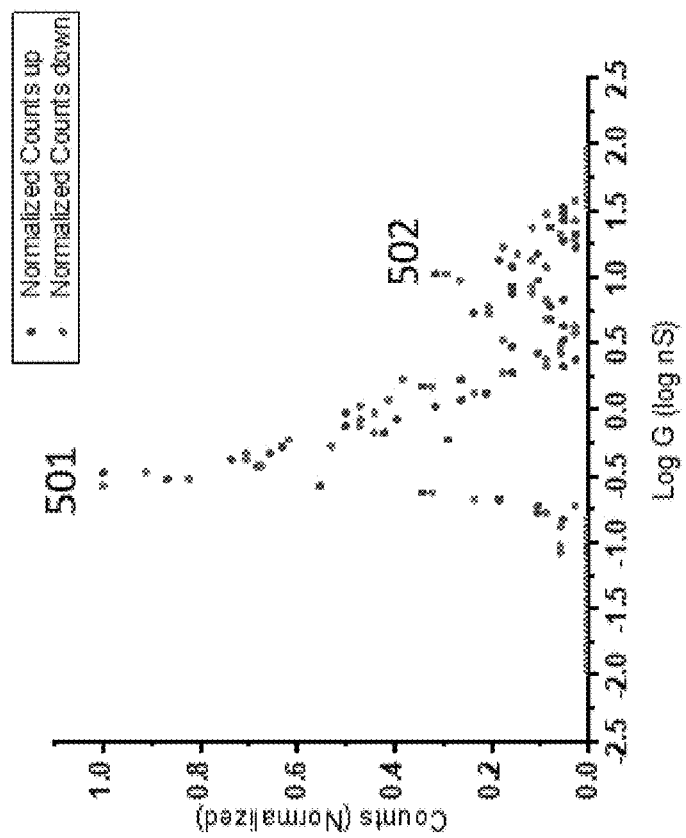
FIG. 5B
FIGS. 5A-5D

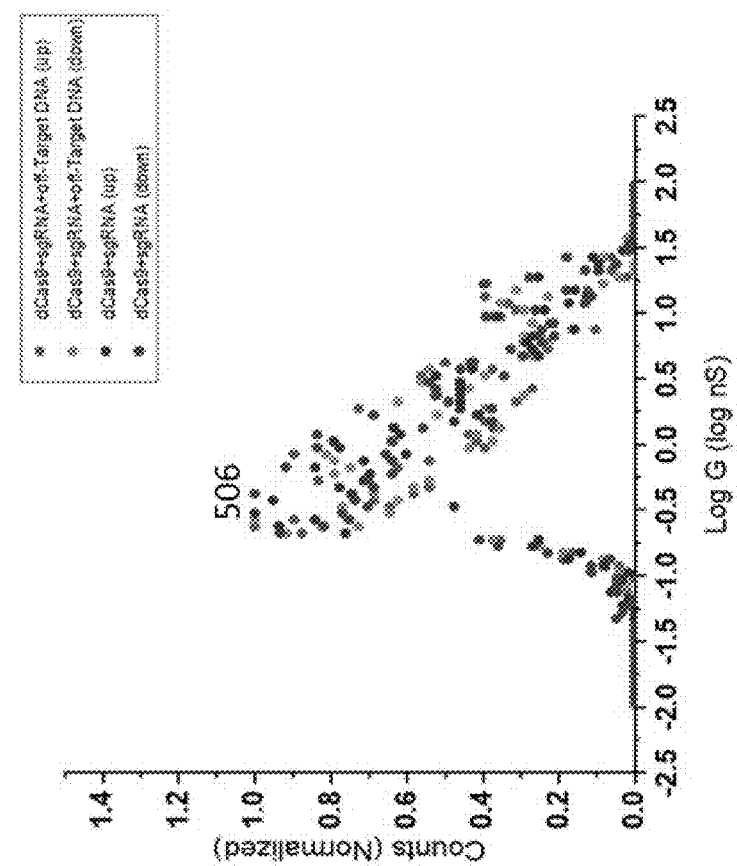
FIG. 5C
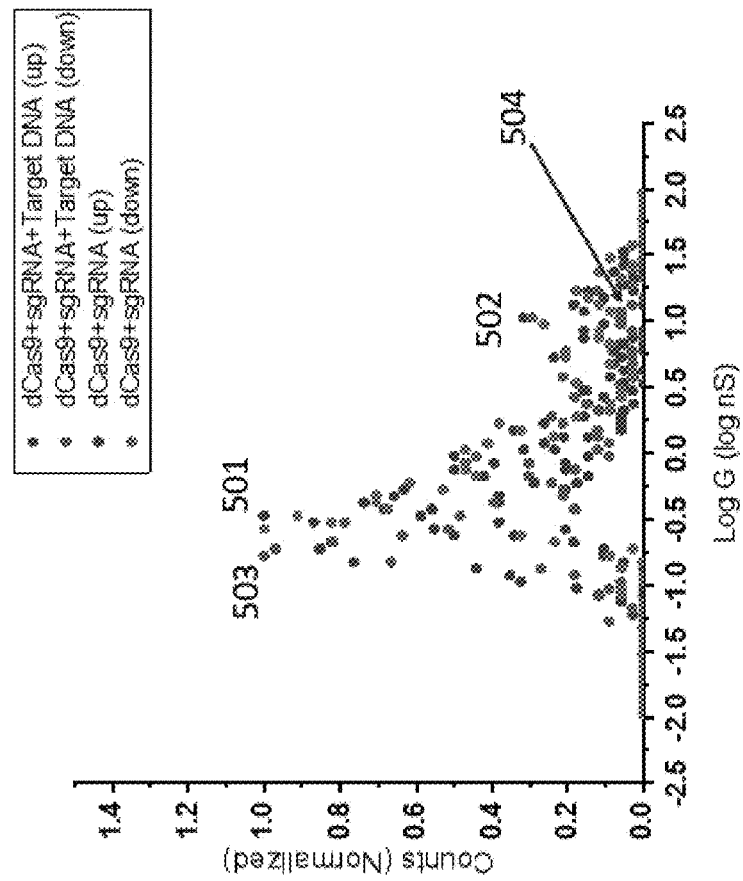
FIG. 5D
FIGS. 5A-5D

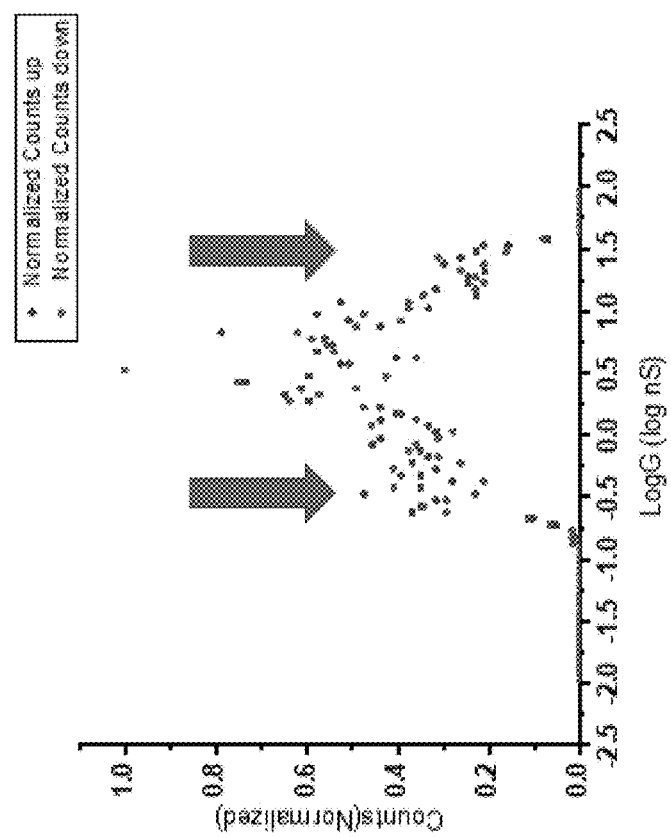
FIG. 7A
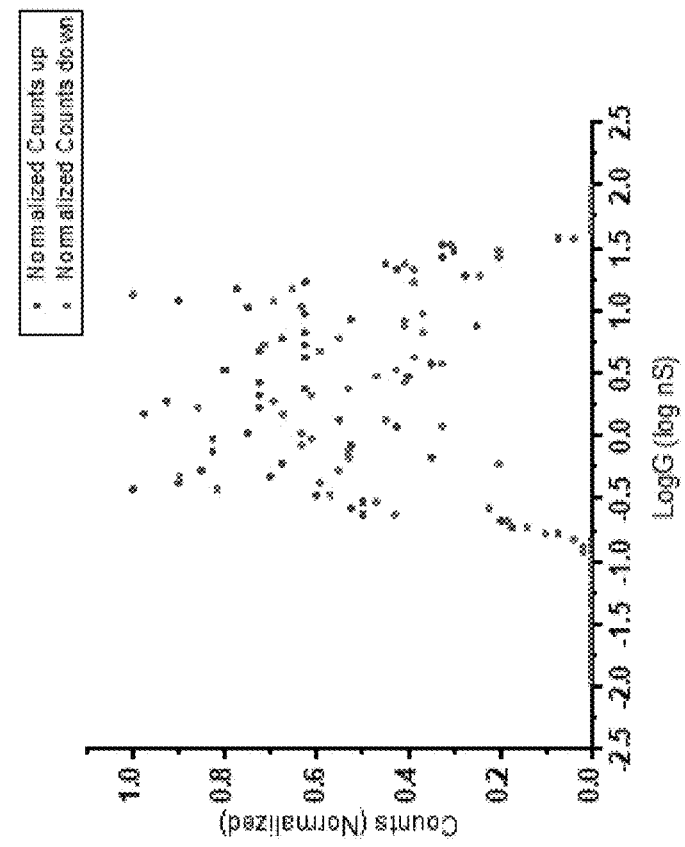
FIG. 7B
FIGS. 7A-7B

SEQUENCE LISTING

<160> NUMBER OF SEQ ID NOS: 14

<210> SEQ ID NO 1
<211> LENGTH: 62
<212> TYPE: PRT
<213> ORGANISM: Artificial Sequence
<220> FEATURE:
<223> OTHER INFORMATION: Synthetic

<400> SEQUENCE: 1

Met Gly Ser Ser His His His His His His Ser Ser Gly Leu Val Pro

```
                1               5                   10                  15
            Arg Gly Ser His Met Ala Ser Met Thr Gly Gly Gln Gln Met Gly Arg
                        20                  25                  30
            Gly Ser Glu Phe Glu Leu Arg Arg Gln Ala Cys Gly Arg Met Gly Leu
                        35                  40                  45
            Asn Asp Ile Phe Glu Ala Gln Lys Ile Glu Trp His Glu Ala
                50                  55                  60

<210> SEQ ID NO 2
<211> LENGTH: 31
<212> TYPE: PRT
<213> ORGANISM: Artificial Sequence
<220> FEATURE:
<223> OTHER INFORMATION: Synthetic

<400> SEQUENCE: 2

Val Gly Leu Asn Asp Ile Phe Glu Ala Gln Lys Ile Glu Trp His Glu
1               5                   10                  15
Ala Gly Gly Ser Gly Gly Gly Leu Glu His His His His His
            20                  25                  30

<210> SEQ ID NO 3
<211> LENGTH: 1994
<212> TYPE: PRT
<213> ORGANISM: Artificial Sequence
<220> FEATURE:
<223> OTHER INFORMATION: Synthetic

<400> SEQUENCE: 3

Met His His His His His His Gly Gly Gly Ser Gly Gly Gly Gly
1               5                   10                  15
Ser Gly Gly Gly Ser Met Ala Glu Ile Gly Thr Gly Phe Pro Phe
            20                  25                  30
Asp Pro His Tyr Val Glu Val Leu Gly Glu Arg Met His Tyr Val Asp
            35                  40                  45
Val Gly Pro Arg Asp Gly Thr Pro Val Leu Phe Leu His Gly Asn Pro
    50                  55                  60
Thr Ser Ser Tyr Val Trp Arg Asn Ile Ile Pro His Val Ala Pro Thr
65                  70                  75                  80
His Arg Cys Ile Ala Pro Asp Leu Ile Gly Met Gly Lys Ser Asp Lys
                        85                  90                  95
Pro Asp Leu Gly Tyr Phe Phe Asp Asp His Val Arg Phe Met Asp Ala
                100                 105                 110
Phe Ile Glu Ala Leu Gly Leu Glu Glu Val Val Leu Val Ile His Asp
            115                 120                 125
Trp Gly Ser Ala Leu Gly Phe His Trp Ala Lys Arg Asn Pro Glu Arg
    130                 135                 140
Val Lys Gly Ile Ala Phe Met Glu Phe Ile Arg Pro Ile Pro Thr Trp
145                 150                 155                 160
Asp Glu Trp Pro Glu Phe Ala Arg Glu Thr Phe Gln Ala Phe Arg Thr
                        165                 170                 175
Thr Asp Val Gly Arg Lys Leu Ile Ile Asp Gln Asn Val Phe Ile Glu
                180                 185                 190
Gly Thr Leu Pro Met Gly Val Val Arg Pro Leu Thr Glu Val Glu Met
            195                 200                 205
Asp His Tyr Arg Glu Pro Phe Leu Asn Pro Val Asp Arg Glu Pro Leu
    210                 215                 220
```

```
Trp Arg Phe Pro Asn Glu Leu Pro Ile Ala Gly Glu Pro Ala Asn Ile
225                 230                 235                 240

Val Ala Leu Val Glu Glu Tyr Met Asp Trp Leu His Gln Ser Pro Val
                245                 250                 255

Pro Lys Leu Leu Phe Trp Gly Thr Pro Gly Val Leu Ile Pro Pro Ala
            260                 265                 270

Glu Ala Ala Arg Leu Ala Lys Ser Leu Pro Asn Cys Lys Ala Val Asp
        275                 280                 285

Ile Gly Pro Gly Leu Asn Leu Leu Gln Glu Asp Asn Pro Asp Leu Ile
    290                 295                 300

Gly Ser Glu Ile Ala Arg Trp Leu Ser Thr Leu Glu Ile Ser Gly Asp
305                 310                 315                 320

Lys Lys Tyr Ser Ile Gly Leu Ala Ile Gly Thr Asn Ser Val Gly Trp
                325                 330                 335

Ala Val Ile Thr Asp Glu Tyr Lys Val Pro Ser Lys Lys Phe Lys Val
            340                 345                 350

Leu Gly Asn Thr Asp Arg His Ser Ile Lys Lys Asn Leu Ile Gly Ala
        355                 360                 365

Leu Leu Phe Asp Ser Gly Glu Thr Ala Glu Ala Thr Arg Leu Lys Arg
370                 375                 380

Thr Ala Arg Arg Arg Tyr Thr Arg Arg Lys Asn Arg Ile Cys Tyr Leu
385                 390                 395                 400

Gln Glu Ile Phe Ser Asn Glu Met Ala Lys Val Asp Asp Ser Phe Phe
                405                 410                 415

His Arg Leu Glu Glu Ser Phe Leu Val Glu Glu Asp Lys Lys His Glu
            420                 425                 430

Arg His Pro Ile Phe Gly Asn Ile Val Asp Glu Val Ala Tyr His Glu
        435                 440                 445

Lys Tyr Pro Thr Ile Tyr His Leu Arg Lys Lys Leu Val Asp Ser Thr
    450                 455                 460

Asp Lys Ala Asp Leu Arg Leu Ile Tyr Leu Ala Leu Ala His Met Ile
465                 470                 475                 480

Lys Phe Arg Gly His Phe Leu Ile Glu Gly Asp Leu Asn Pro Asp Asn
                485                 490                 495

Ser Asp Val Asp Lys Leu Phe Ile Gln Leu Val Gln Thr Tyr Asn Gln
            500                 505                 510

Leu Phe Glu Glu Asn Pro Ile Asn Ala Ser Gly Val Asp Ala Lys Ala
        515                 520                 525

Ile Leu Ser Ala Arg Leu Ser Lys Ser Arg Arg Leu Glu Asn Leu Ile
530                 535                 540

Ala Gln Leu Pro Gly Glu Lys Lys Asn Gly Leu Phe Gly Asn Leu Ile
545                 550                 555                 560

Ala Leu Ser Leu Gly Leu Thr Pro Asn Phe Lys Ser Asn Phe Asp Leu
                565                 570                 575

Ala Glu Asp Ala Lys Leu Gln Leu Ser Lys Asp Thr Tyr Asp Asp Asp
            580                 585                 590

Leu Asp Asn Leu Leu Ala Gln Ile Gly Asp Gln Tyr Ala Asp Leu Phe
        595                 600                 605

Leu Ala Ala Lys Asn Leu Ser Asp Ala Ile Leu Leu Ser Asp Ile Leu
610                 615                 620

Arg Val Asn Thr Glu Ile Thr Lys Ala Pro Leu Ser Ala Ser Met Ile
625                 630                 635                 640

Lys Arg Tyr Asp Glu His His Gln Asp Leu Thr Leu Leu Lys Ala Leu
```

-continued

```
                645                 650                 655
    Val Arg Gln Gln Leu Pro Glu Lys Tyr Lys Glu Ile Phe Phe Asp Gln
                        660                 665                 670

Ser Lys Asn Gly Tyr Ala Gly Tyr Ile Asp Gly Gly Ala Ser Gln Glu
                675                 680                 685

Glu Phe Tyr Lys Phe Ile Lys Pro Ile Leu Glu Lys Met Asp Gly Thr
    690                 695                 700

Glu Glu Leu Leu Val Lys Leu Asn Arg Glu Asp Leu Leu Arg Lys Gln
    705                 710                 715                 720

Arg Thr Phe Asp Asn Gly Ser Ile Pro His Gln Ile His Leu Gly Glu
                        725                 730                 735

Leu His Ala Ile Leu Arg Arg Gln Glu Asp Phe Tyr Pro Phe Leu Lys
                    740                 745                 750

Asp Asn Arg Glu Lys Ile Glu Lys Ile Leu Thr Phe Arg Ile Pro Tyr
                755                 760                 765

Tyr Val Gly Pro Leu Ala Arg Gly Asn Ser Arg Phe Ala Trp Met Thr
    770                 775                 780

Arg Lys Ser Glu Glu Thr Ile Thr Pro Trp Asn Phe Glu Glu Val Val
    785                 790                 795                 800

Asp Lys Gly Ala Ser Ala Gln Ser Phe Ile Glu Arg Met Thr Asn Phe
                    805                 810                 815

Asp Lys Asn Leu Pro Asn Glu Lys Val Leu Pro Lys His Ser Leu Leu
                820                 825                 830

Tyr Glu Tyr Phe Thr Val Tyr Asn Glu Leu Thr Lys Val Lys Tyr Val
                    835                 840                 845

Thr Glu Gly Met Arg Lys Pro Ala Phe Leu Ser Gly Glu Gln Lys Lys
    850                 855                 860

Ala Ile Val Asp Leu Leu Phe Lys Thr Asn Arg Lys Val Thr Val Lys
    865                 870                 875                 880

Gln Leu Lys Glu Asp Tyr Phe Lys Lys Ile Glu Cys Phe Asp Ser Val
                    885                 890                 895

Glu Ile Ser Gly Val Glu Asp Arg Phe Asn Ala Ser Leu Gly Thr Tyr
                900                 905                 910

His Asp Leu Leu Lys Ile Ile Lys Asp Lys Asp Phe Leu Asp Asn Glu
                    915                 920                 925

Glu Asn Glu Asp Ile Leu Glu Asp Ile Val Leu Thr Leu Thr Leu Phe
    930                 935                 940

Glu Asp Arg Glu Met Ile Glu Glu Arg Leu Lys Thr Tyr Ala His Leu
    945                 950                 955                 960

Phe Asp Asp Lys Val Met Lys Gln Leu Lys Arg Arg Arg Tyr Thr Gly
                    965                 970                 975

Trp Gly Arg Leu Ser Arg Lys Leu Ile Asn Gly Ile Arg Asp Lys Gln
                980                 985                 990

Ser Gly Lys Thr Ile Leu Asp Phe Leu Lys Ser Asp Gly Phe Ala Asn
                995                 1000                1005

Arg Asn Phe Met Gln Leu Ile His Asp Asp Ser Leu Thr Phe Lys
            1010                1015                1020

Glu Asp Ile Gln Lys Ala Gln Val Ser Gly Gln Gly Asp Ser Leu
            1025                1030                1035

His Glu His Ile Ala Asn Leu Ala Gly Ser Pro Ala Ile Lys Lys
            1040                1045                1050

Gly Ile Leu Gln Thr Val Lys Val Val Asp Glu Leu Val Lys Val
            1055                1060                1065
```

```
Met Gly Arg His Lys Pro Glu Asn Ile Val Ile Glu Met Ala Arg
    1070                1075                1080

Glu Asn Gln Thr Thr Gln Lys Gly Gln Lys Asn Ser Arg Glu Arg
    1085                1090                1095

Met Lys Arg Ile Glu Glu Gly Ile Lys Glu Leu Gly Ser Gln Ile
    1100                1105                1110

Leu Lys Glu His Pro Val Glu Asn Thr Gln Leu Gln Asn Glu Lys
    1115                1120                1125

Leu Tyr Leu Tyr Tyr Leu Gln Asn Gly Arg Asp Met Tyr Val Asp
    1130                1135                1140

Gln Glu Leu Asp Ile Asn Arg Leu Ser Asp Tyr Asp Val Asp Ala
    1145                1150                1155

Ile Val Pro Gln Ser Phe Leu Lys Asp Asp Ser Ile Asp Asn Lys
    1160                1165                1170

Val Leu Thr Arg Ser Asp Lys Asn Arg Gly Lys Ser Asp Asn Val
    1175                1180                1185

Pro Ser Glu Glu Val Val Lys Lys Met Lys Asn Tyr Trp Arg Gln
    1190                1195                1200

Leu Leu Asn Ala Lys Leu Ile Thr Gln Arg Lys Phe Asp Asn Leu
    1205                1210                1215

Thr Lys Ala Glu Arg Gly Gly Leu Ser Glu Leu Asp Lys Ala Gly
    1220                1225                1230

Phe Ile Lys Arg Gln Leu Val Glu Thr Arg Gln Ile Thr Lys His
    1235                1240                1245

Val Ala Gln Ile Leu Asp Ser Arg Met Asn Thr Lys Tyr Asp Glu
    1250                1255                1260

Asn Asp Lys Leu Ile Arg Glu Val Lys Val Ile Thr Leu Lys Ser
    1265                1270                1275

Lys Leu Val Ser Asp Phe Arg Lys Asp Phe Gln Phe Tyr Lys Val
    1280                1285                1290

Arg Glu Ile Asn Asn Tyr His His Ala His Asp Ala Tyr Leu Asn
    1295                1300                1305

Ala Val Val Gly Thr Ala Leu Ile Lys Lys Tyr Pro Lys Leu Glu
    1310                1315                1320

Ser Glu Phe Val Tyr Gly Asp Tyr Lys Val Tyr Asp Val Arg Lys
    1325                1330                1335

Met Ile Ala Lys Ser Glu Gln Glu Ile Gly Lys Ala Thr Ala Lys
    1340                1345                1350

Tyr Phe Phe Tyr Ser Asn Ile Met Asn Phe Phe Lys Thr Glu Ile
    1355                1360                1365

Thr Leu Ala Asn Gly Glu Ile Arg Lys Arg Pro Leu Ile Glu Thr
    1370                1375                1380

Asn Gly Glu Thr Gly Glu Ile Val Trp Asp Lys Gly Arg Asp Phe
    1385                1390                1395

Ala Thr Val Arg Lys Val Leu Ser Met Pro Gln Val Asn Ile Val
    1400                1405                1410

Lys Lys Thr Glu Val Gln Thr Gly Gly Phe Ser Lys Glu Ser Ile
    1415                1420                1425

Leu Pro Lys Arg Asn Ser Asp Lys Leu Ile Ala Arg Lys Lys Asp
    1430                1435                1440

Trp Asp Pro Lys Lys Tyr Gly Gly Phe Asp Ser Pro Thr Val Ala
    1445                1450                1455
```

```
Tyr Ser Val Leu Val Val Ala Lys Val Glu Lys Gly Lys Ser Lys
    1460            1465                1470                1475

Lys Leu Lys Ser Val Lys Glu Leu Leu Gly Ile Thr Ile Met Glu
                1480                1485

Arg Ser Ser Phe Glu Lys Asn Pro Ile Asp Phe Leu Glu Ala Lys
    1490                1495                1500

Gly Tyr Lys Glu Val Lys Lys Asp Leu Ile Ile Lys Leu Pro Lys
    1505                1510                1515

Tyr Ser Leu Phe Glu Leu Glu Asn Gly Arg Lys Arg Met Leu Ala
    1520                1525                1530

Ser Ala Gly Glu Leu Gln Lys Gly Asn Glu Leu Ala Leu Pro Ser
    1535                1540                1545

Lys Tyr Val Asn Phe Leu Tyr Leu Ala Ser His Tyr Glu Lys Leu
    1550                1555                1560

Lys Gly Ser Pro Glu Asp Asn Glu Gln Lys Gln Leu Phe Val Glu
    1565                1570                1575

Gln His Lys His Tyr Leu Asp Glu Ile Ile Glu Gln Ile Ser Glu
    1580                1585                1590

Phe Ser Lys Arg Val Ile Leu Ala Asp Ala Asn Leu Asp Lys Val
    1595                1600                1605

Leu Ser Ala Tyr Asn Lys His Arg Asp Lys Pro Ile Arg Glu Gln
    1610                1615                1620

Ala Glu Asn Ile Ile His Leu Phe Thr Leu Thr Asn Leu Gly Ala
    1625                1630                1635

Pro Ala Ala Phe Lys Tyr Phe Asp Thr Thr Ile Asp Arg Lys Arg
    1640                1645                1650

Tyr Thr Ser Thr Lys Glu Val Leu Asp Ala Thr Leu Ile His Gln
    1655                1660                1665

Ser Ile Thr Gly Leu Tyr Glu Thr Arg Ile Asp Leu Ser Gln Leu
    1670                1675                1680

Gly Gly Asp Ser Arg Ala Asp Pro Lys Lys Lys Arg Lys Val Met
    1685                1690                1695

Ala Glu Ile Gly Thr Gly Phe Pro Phe Asp Pro His Tyr Val Glu
    1700                1705                1710

Val Leu Gly Glu Arg Met His Tyr Val Asp Val Gly Pro Arg Asp
    1715                1720                1725

Gly Thr Pro Val Leu Phe Leu His Gly Asn Pro Thr Ser Ser Tyr
    1730                1735                1740

Val Trp Arg Asn Ile Ile Pro His Val Ala Pro Thr His Arg Cys
    1745                1750                1755

Ile Ala Pro Asp Leu Ile Gly Met Gly Lys Ser Asp Lys Pro Asp
    1760                1765                1770

Leu Gly Tyr Phe Phe Asp Asp His Val Arg Phe Met Asp Ala Phe
    1775                1780                1785

Ile Glu Ala Leu Gly Leu Glu Glu Val Val Leu Val Ile His Asp
    1790                1795                1800

Trp Gly Ser Ala Leu Gly Phe His Trp Ala Lys Arg Asn Pro Glu
    1805                1810                1815

Arg Val Lys Gly Ile Ala Phe Met Glu Phe Ile Arg Pro Ile Pro
    1820                1825                1830

Thr Trp Asp Glu Trp Pro Glu Phe Ala Arg Glu Thr Phe Gln Ala
    1835                1840                1845

Phe Arg Thr Thr Asp Val Gly Arg Lys Leu Ile Ile Asp Gln Asn
```

| | | | | | | | | |
|---|---|---|---|---|---|---|---|---|
| | | 1850 | | | 1855 | | | 1860 |

Val Phe Ile Glu Gly Thr Leu Pro Met Gly Val Val Arg Pro Leu
 1865                    1870                        1875

Thr Glu Val Glu Met Asp His Tyr Arg Glu Pro Phe Leu Asn Pro
 1880                    1885                        1890

Val Asp Arg Glu Pro Leu Trp Arg Phe Pro Asn Glu Leu Pro Ile
 1895                    1900                        1905

Ala Gly Glu Pro Ala Asn Ile Val Ala Leu Val Glu Glu Tyr Met
 1910                    1915                        1920

Asp Trp Leu His Gln Ser Pro Val Pro Lys Leu Leu Phe Trp Gly
 1925                    1930                        1935

Thr Pro Gly Val Leu Ile Pro Pro Ala Glu Ala Ala Arg Leu Ala
 1940                    1945                        1950

Lys Ser Leu Pro Asn Cys Lys Ala Val Asp Ile Gly Pro Gly Leu
 1955                    1960                        1965

Asn Leu Leu Gln Glu Asp Asn Pro Asp Leu Ile Gly Ser Glu Ile
 1970                    1975                        1980

Ala Arg Trp Leu Ser Thr Leu Glu Ile Ser Gly
 1985                    1990

<210> SEQ ID NO 4
<211> LENGTH: 62
<212> TYPE: RNA
<213> ORGANISM: Artificial Sequence
<220> FEATURE:
<223> OTHER INFORMATION: Synthetic

<400> SEQUENCE: 4
ucuaaagccg aaaaacccug guuuuagagc uagaaauagc aaguuaaaau aaggcuaguc    60
cg                                                                   62

<210> SEQ ID NO 5
<211> LENGTH: 62
<212> TYPE: RNA
<213> ORGANISM: Artificial Sequence
<220> FEATURE:
<223> OTHER INFORMATION: Synthetic

<400> SEQUENCE: 5
gcuacacuac gugcccgccg guuuuagagc uagaaauagc aaguuaaaau aaggcuaguc    60
cg                                                                   62

<210> SEQ ID NO 6
<211> LENGTH: 62
<212> TYPE: RNA
<213> ORGANISM: Artificial Sequence
<220> FEATURE:
<223> OTHER INFORMATION: Synthetic

<400> SEQUENCE: 6
uugcgcguac gcguuccaug guuuuagagc uagaaauagc aaguuaaaau aaggcuaguc    60
cg                                                                   62

<210> SEQ ID NO 7
<211> LENGTH: 62
<212> TYPE: RNA
<213> ORGANISM: Artificial Sequence
<220> FEATURE:
<223> OTHER INFORMATION: Synthetic

<400> SEQUENCE: 7
caauacgaag auguccacga guuuuagagc uagaaauagc aaguuaaaau aaggcuaguc    60
cg                                                                  62

<210> SEQ ID NO 8
<211> LENGTH: 62
<212> TYPE: RNA
<213> ORGANISM: Artificial Sequence
<220> FEATURE:
<223> OTHER INFORMATION: Synthetic

<400> SEQUENCE: 8
aguuguggca ucuccugaug guuuuagagc uagaaauagc aaguuaaaau aaggcuaguc    60
cg                                                                  62

<210> SEQ ID NO 9
<211> LENGTH: 62
<212> TYPE: RNA
<213> ORGANISM: Artificial Sequence
<220> FEATURE:
<223> OTHER INFORMATION: Synthetic

<400> SEQUENCE: 9
gggcgcgauc aaaacaacgu guuuuagagc uagaaauagc aaguuaaaau aaggcuaguc    60
cg                                                                  62

<210> SEQ ID NO 10
<211> LENGTH: 62
<212> TYPE: RNA
<213> ORGANISM: Artificial Sequence
<220> FEATURE:
<223> OTHER INFORMATION: Synthetic

<400> SEQUENCE: 10
ccaccuauag gggaacacug guuuuagagc uagaaauagc aaguuaaaau aaggcuaguc    60
cg                                                                  62

<210> SEQ ID NO 11
<211> LENGTH: 62
<212> TYPE: RNA
<213> ORGANISM: Artificial Sequence
<220> FEATURE:
<223> OTHER INFORMATION: Synthetic

<400> SEQUENCE: 11
uaaggaguac cuacgacaug guuuuagagc uagaaauagc aaguuaaaau aaggcuaguc    60
cg                                                                  62

<210> SEQ ID NO 12
<211> LENGTH: 62
<212> TYPE: RNA
<213> ORGANISM: Artificial Sequence
<220> FEATURE:
<223> OTHER INFORMATION: Synthetic

<400> SEQUENCE: 12
gcaacaguua cugcgacgug guuuuagagc uagaaauagc aaguuaaaau aaggcuaguc    60
cg                                                                  62

<210> SEQ ID NO 13
<211> LENGTH: 62

```
<212> TYPE: RNA
<213> ORGANISM: Artificial Sequence
<220> FEATURE:
<223> OTHER INFORMATION: Synthetic

<400> SEQUENCE: 13
gagcuucagc uaccgcuacg guuuuagagc uagaaauagc aaguuaaaau aaggcuaguc      60
cg                                                                   62

<210> SEQ ID NO 14
<211> LENGTH: 62
<212> TYPE: RNA
<213> ORGANISM: Artificial Sequence
<220> FEATURE:
<223> OTHER INFORMATION: Synthetic

<400> SEQUENCE: 14
guacugauaa ggcugacuug guuuuagagc uagaaauagc aaguuaaaau aaggcuaguc      60
cg                                                                   62
```

SINGLE-MOLECULE ELECTRONIC SEQUENCE DETECTOR AND METHODS OF USE

RELATED APPLICATIONS

This application claims priority to and the benefit of U.S. Provisional Patent Application No. 63/011,799 filed Feb. 28, 2020, which is incorporated herein by reference in its entirety for all purposes.

GOVERNMENT SUPPORT

This invention was made with government support under HG010522 awarded by the National Institutes of Health. The government has certain rights in the invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 21,644 Byte ASCII (Text) file named "2021-04-15_38883-601_SQL_ST25.txt," created on Apr. 15, 2021.

FIELD

The present disclosure provides devices, systems, and methods related to single molecule detection. In particular, the present disclosure provides devices and methods for sequence-specific detection of a nucleic acid target using current fluctuations as a readout for protein binding to the nucleic acid target. As described herein, certain aspects of the bioelectronic devices and method described herein can be used to detect and identify any nucleic acid target for the purpose of diagnosis and/or treatment.

BACKGROUND

The clustered regularly interspaced short palindromic repeat (CRISPR)-associated Cas nucleases are a group of programmable ribonucleoproteins (RNPs) involved in adaptive bacterial immunity. Specific DNA and RNA target motifs of 20 nucleotides (in most cases) are defined by a CRISPR RNA (crRNA), containing the target sequence and a trans-activating crRNA (tracrRNA) of constant sequence which fold to form a stem-loop structure that binds Cas9 (or other CRISPR associated proteins also known as Cas nucleases). Cas9 CRISPR complex interacts with its target sequence by scanning a sample (e.g., a genomic sample), unwinding duplex DNA and binding upstream of a protospacer adjacent motif until it finds and binds to the target sequence that is complementary to the single-guide RNA molecule (sgRNA) within the dRNP. The RNP, programmed by a sgRNA is an efficient method for searching for a very specific target sequence, in applications such as genotyping, both germline and somatic, HLA typing, medical genetics for targeted genotyping, circulating tumor DNA, fetal DNA testing, infectious disease detection and monitoring; any nucleic acid sensing, criminology and biodefense.

The function of the wild-type RNP is to cleave the target DNA. But by using a modified RNP, in which nuclease activity is inhibited, the complex stops at the target sequence, trapping target DNA. These nuclease deficient Cas proteins are denoted dCas, for example dCas9. A device in which many RNP's are bound to the channel of a graphene field effect transistor has been developed (e.g., trapping the target DNA results in increased charge on the surface of the graphene channel, detected via a change in current passing through the channel of the graphene FET). However, this detection is disadvantageous because detection is analog (registered as a continuous change in current), and calibration is required for quantification of the target DNA. Thus, currently available devices and systems are insufficient to detect target DNA at the single molecule level.

SUMMARY

Embodiments of the present disclosure include a bioelectronic device for detecting a target nucleic acid. In accordance with these embodiments, the device includes a first electrode, a second electrode, and at least one CRISPR-associated protein. In some embodiments, the CRISPR-associated protein is modified to form a chemical bond with at least one of the first and the second electrodes.

In some embodiments, the modification allows an electrical current to pass through the CRISPR-associated protein, and the binding of the CRISPR-associated protein to a target nucleic acid causes a shift in the current.

In some embodiments, the CRISPR-associated protein is a Cas family member protein selected from the group consisting of Cas1, Cas2, Cas3, Cas4, Cas5, Cas6, Cas7, Cas8, Cas10, Cas12, Cas13, Cas14, their nuclease-deficient dCas equivalents, and any variants or derivatives thereof. In some embodiments, the CRISPR-associate protein is Cas9 protein or dCas9.

In some embodiments, the modification comprises adding a linker. In some embodiments, the modification comprises adding at least two linkers on at least two sites on the CRISPR-associated protein, with the at least two linkers attached to each of the first and second electrodes. In some embodiments, one linker of the at least two linkers is attached to site on the CRISPR-associated protein, and another linker of the at least two linkers is attached to a different site on the CRISPR-associated protein.

In some embodiments, the linker is attached to an inactive region of the CRISPR-associated protein via a covalent chemical bond. In some embodiments, the modification comprises biotinylating the CRISPR-associate protein. In some embodiments, the linker comprises thio-streptavidin. In some embodiments, the CRISPR-associate protein and the first and second electrodes are biotinylated, and the linker comprises a streptavidin molecule having at least two biotin binding sites.

In some embodiments, the modification comprises a HaloTag fusion protein and a chloroalkane linker.

In some embodiments, the first and/or the second electrode comprises gold, palladium, platinum, silver, copper, or any alloys thereof.

In some embodiments, the first electrode comprises a dielectric layer at least partially covering a top surface of the first electrode.

In some embodiments, the thickness of the dielectric layer is from about 1 nm to about 50 nm.

In some embodiments, the first electrode and second electrode are positioned so that between about a 1 nm and about a 50 nm gap is formed between the two electrodes. In some embodiments, the gap is from about 2 to about 8 nm.

Embodiments of the present disclosure also include a method of detecting a target nucleic acid using any of the bioelectronic devices described herein. In accordance with these embodiments, the method includes combining the bioelectronic device and the target nucleic acid with a guide RNA, applying a voltage bias between the first and the second electrode that is 100 mV or less, and detecting a shift in current upon binding of the CRISPR-associated protein and the guide RNA to the target nucleic acid.

In some embodiments of the method, the guide RNA is complementary to a portion of the target nucleic acid.

In some embodiments of the method, the shift in current comprises a decrease in current as compared to the current when the CRISPR-associated protein is not bound to the target nucleic acid.

In some embodiments of the method, the target nucleic acid is contained in or derived from a sample from a subject.

In some embodiments of the method, the detection of the shift in current indicates that the target nucleic acid is present in the sample.

In some embodiments of the method, the sample is selected from the group consisting of a blood sample, a serum sample, a plasma sample, a saliva sample, a urine sample, a stool sample, and a mucosal sample.

In some embodiments of the method, the target nucleic acid is DNA or RNA.

In some embodiments of the method, the target nucleic acid is derived from or associated with a pathogenic organism. In some embodiments of the method, the target nucleic acid is derived from, associated with, or indicative of a disease or condition. In some embodiments of the method, the target nucleic acid is derived from or associated with an engineered organism. In some embodiments of the method, the target nucleic acid is derived from or associated with a SARS-CoV-2 infection.

Embodiments of the present disclosure also include a system comprising a plurality of the bioelectronic devices described herein. In some embodiments of the system, the plurality of bioelectronic devices are configured to detect more than one target nucleic acid based on corresponding guide RNA sequences.

BRIEF DESCRIPTION OF THE DRAWINGS

FIGS. 5A-5D: FIG. 5A includes representative graphical data of the distribution of single molecule conductance for dCas9+sgRNA without target DNA. The plot provides the probability of a conductance value on the vertical axis, versus the logarithm (base 10) of the measured conductance; the two peaks correspond to two specific connections (higher conductance) and one specific connection (lower conductance). FIG. 5B includes representative graphical data of the distribution of single molecule conductance for dCas9+sgRNA with target DNA present. FIG. 5C includes representative graphical data of distributions with (green points), and without (blue points), target DNA superimposed. In the presence of target DNA, the highest conduction peak is greatly diminished and the lower peak moves to smaller values of conductance. FIG. 5D includes representative graphical data of the same superimposition of distributions without DNA (blue points) and with off-target DNA (green points). The distribution is unchanged.

FIGS. 7A-7B: Representative graphical data of the distribution of conductance for many dCas9 molecules bound with sgRNA (FIG. 7A), including the distribution measured after target DNA was added; the arrows point to regions of significant changes in conductance (FIG. 7B).

DETAILED DESCRIPTION

Figure 1:
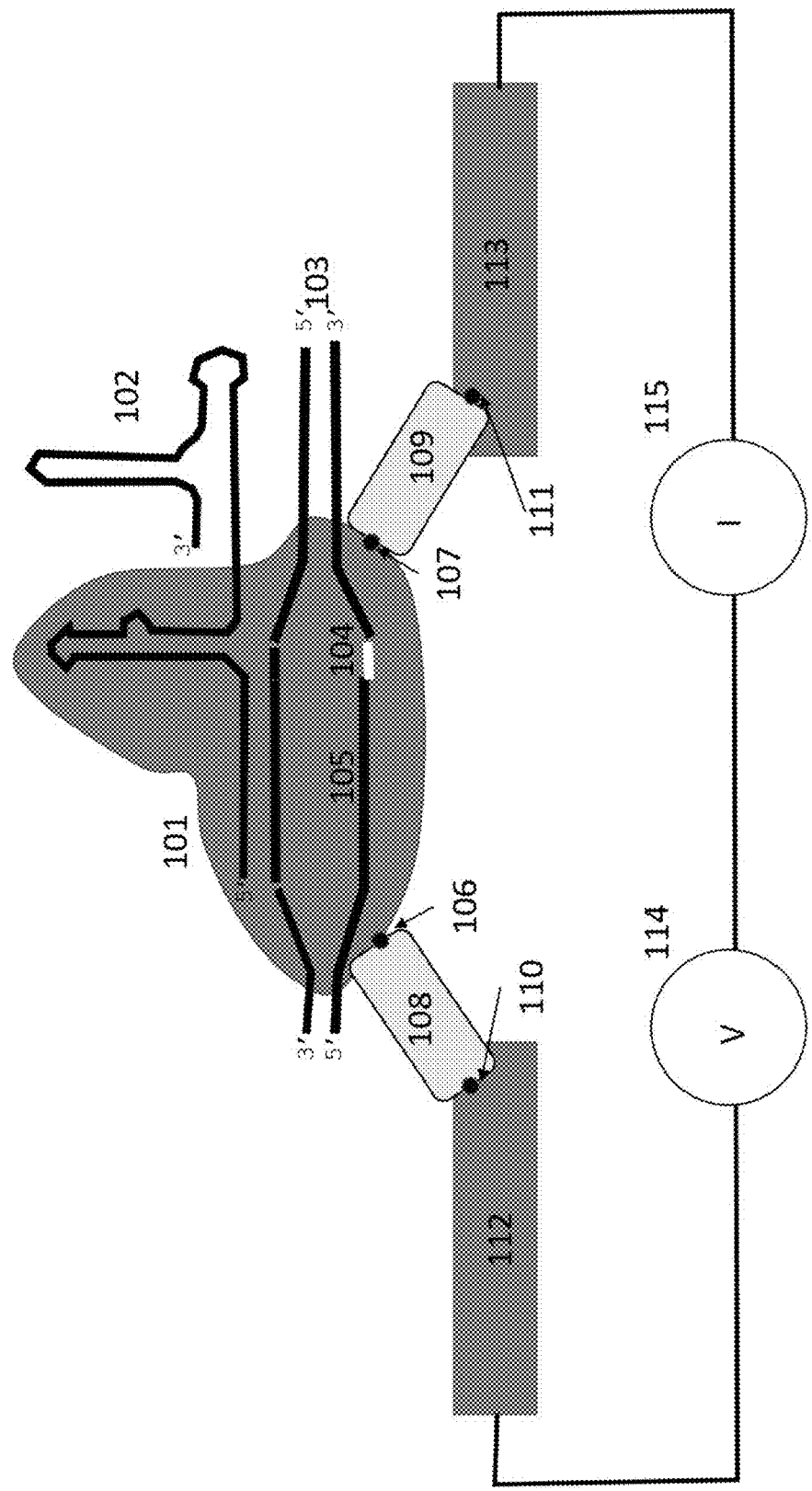
FIG. 1: Representative schematic diagram of an exemplary CRISPR-associated protein integrated into an electronic recording circuit (e.g., bioelectronic device), according to one embodiment of the present disclosure.

Section headings as used in this section and the entire disclosure herein are merely for organizational purposes and are not intended to be limiting.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present disclosure. All publications, patent applications, patents and other references mentioned herein are incorporated by reference in their entirety. The materials, methods, and examples disclosed herein are illustrative only and not intended to be limiting.

As noted herein, the disclosed embodiments have been presented for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, compositions, systems and apparatuses/devices which may further include any and all elements from any other disclosed methods, compositions, systems, and devices, including any and all elements corresponding to detecting protein activity. In other words, elements from one or another disclosed embodiments may be interchangeable with elements from other disclosed embodiments. Moreover, some further embodiments may be realized by combining one and/or another feature disclosed herein with methods, compositions, systems and devices, and one or more features thereof, disclosed in materials incorporated by reference. In addition, one or more features/elements of disclosed embodiments may be removed and still result in patentable subject matter (and thus, resulting in yet more embodiments of the subject disclosure). Furthermore, some embodiments correspond to methods, compositions, systems, and devices which specifically lack one and/or another element, structure, and/or steps (as applicable), as compared to teachings of the prior art, and therefore represent patentable subject matter and are distinguishable therefrom (i.e. claims directed to such embodiments may contain negative limitations to note the lack of one or more features prior art teachings).

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of" or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein, "CAS proteins" or "CAS family of proteins" includes mammalian cellular apoptosis susceptibility (CAS) proteins. CAS is involved in both cellular apoptosis and proliferation. Apoptosis is inhibited in CAS-depleted cells, while the expression of CAS correlates to the degree of cellular proliferation. In the nucleus, CAS acts as a nuclear transport factor in the importin pathway. The importin pathway mediates the nuclear transport of several proteins that are necessary for mitosis and further progression. CAS is thought to affect the cell cycle through its effect on the nuclear transport of these proteins. Since apoptosis also requires the nuclear import of several proteins (such as P53 and transcription factors), it has been suggested that CAS also enables apoptosis by facilitating the nuclear import of at least a subset of these essential proteins. Members of the CAS family of proteins have two domains. An N-terminal Cse1 domain, which contains HEAT repeats, and a C-terminal domain. In some embodiments, as described further herein, CAS proteins can include, but are not limited to, Cas1, Cas2, Cas3, Cas4, Cas5, Cas6, Cas7, Cas8, Cas10, Cas12, Cas13, Cas14, as week as their nuclease-deficient dCas equivalents, and any variants or derivatives thereof (e.g., referred to herein as "CRISPR-associated" protein(s)). In some embodiments, the CAS protein is Cas9 or dCas9, which is a nuclease, an enzyme specialized for cutting DNA, with two active cutting sites (HNH and RuvC), one for each strand of the double helix.

As used herein, "modification," "chemical modification," or "chemically modified" generally refers to any of a number of various processes involving the alteration of the chemical constituent or structure of molecules. For example, a CRISPR-associated protein can be chemically modified to form a chemical bond with a first electrode and a second electrode. In one example, a chemically-modified electrode is an electrode that has a surface chemically converted to change the electrode's properties, such as its physical, chemical, electrochemical, optical, electrical, and/or transport characteristics. As provided herein, the chemical modification can also involve chemically altering a CRISPR-associated protein so that it is compatible with a linker that binds to an electrode (e.g., biotin/streptavidin, HaloTag, and the like). In other embodiments, a modification can be generated via protein synthesis. For example, a CRISPR-associated protein can be designed to comprise one or more modifications (e.g., a linker) when synthesized from a polynucleotide that encodes the protein and the modification (e.g. linker).

As used herein, "contact" and "contacting" can include placement in direct physical association, including both a solid and liquid form. "Contacting" can include a specific chemical contact between two different substances (e.g., covalent bond, or non-covalent bond having specific ligand interaction with specific amino acid residues).

As used herein, "complementarity" or "complementary" generally refers to the ability of a nucleic acid to form hydrogen bond(s) with another nucleic acid sequence by either traditional Watson-Crick base pairing or other nontraditional types. A percent complementarity indicates the percentage of residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" generally indicates that all the contiguous residues of a nucleic acid sequence will hydrogen bond with the same number of contiguous residues in a second nucleic acid sequence. "Substantially complementary" as used herein refers to a degree of complementarity that is at least 60%, 65%, 70%, 75%, 80%, 85%, 90%, 95%, 97%, 98%, 99%, or 100% over a region of 8, 9, 10, 11, 12, 13, 14, 15, 16, 17, 18, 19, 20, 21, 22, 23, 24, 25, 30, 35, 40, 45, 50, or more nucleotides, or refers to two nucleic acids that hybridize under stringent conditions.

As used herein, "CRISPR" (clustered regularly interspaced short palindromic repeats) refers to a DNA loci containing short repetitions of base sequences. Each repetition is followed by short segments of "spacer DNA" from previous exposures to a virus. CRISPRs are found in approximately 40% of sequenced bacteria genomes and 90% of sequenced archaea. CRISPRs are often associated with Cas genes that code for proteins related to CRISPRs. The CRISPR/Cas system is a prokaryotic immune system that confers resistance to foreign genetic elements such as plasmids and phages and provides a form of acquired immunity. CRISPR spacers recognize and cut these exogenous genetic elements in a manner analogous to RNAi in eukaryotic organisms. The CRISPR/Cas system can be used for gene editing (adding, disrupting, or changing the sequence of specific genes) and gene regulation in species. By delivering a Cas protein, such as a Cas9 protein, and appropriate guide RNAs into a cell, the organism's genome can be cut at any desired location. A CRISPR-associated protein is a protein associated with CRISPRs.

As used herein, "expression" generally refers to the process by which a polynucleotide is transcribed from a DNA template (such as into and mRNA or other RNA transcript) and/or the process by which a transcribed mRNA is subsequently translated into peptides, polypeptides, or proteins. Transcripts and encoded polypeptides may be collectively referred to as "gene product." If the polynucleotide is derived from genomic DNA, expression may include splicing of the mRNA in a eukaryotic cell.

As used herein, "guide sequence" includes any polynucleotide sequence having sufficient complementarity with a target polynucleotide sequence to hybridize with the target sequence and direct sequence-specific binding of a CRISPR complex to the target sequence. In some embodiments, the degree of complementarity between a guide sequence and its corresponding target sequence, when optimally aligned using a suitable alignment algorithm, is about or more than about 50%, 60%, 75%, 80%, 85%, 90%, 95%, 97.5%, 99%, or more. Optimal alignment may be determined with the use of any suitable algorithm for aligning sequences, non-limiting example of which include the Smith-Waterman algorithm, the Needleman-Wunsch algorithm, algorithms based on the Burrows-Wheeler Transform (e.g., the Burrows Wheeler Aligner), ClustalW, Clustal X, BLAT, Novoalign (Novocraft Technologies, ELAND (Illumina, San Diego, Calif.), SOAP (available at soap.genomics.org.cn), and Maq (available at maq.sourceforge.net). In some embodiments, a guide sequence is about or more than about 5, 10, 11, 12, 13, 14, 15, 16, 17, 18, 19, 20, 21, 22, 23, 24, 25, 26, 27, 28, 29, 30, 35, 40, 45, 50, 75, or more nucleotides in length. In some embodiments, a guide sequence is less than about 75, 50, 45, 40, 35, 30, 25, 20, 15, 12, or fewer nucleotides in length. The ability of a guide sequence to direct sequence-specific binding of a CRISPR complex to a target sequence may be assessed by any suitable assay. For example, the components of a CRISPR system sufficient to form a CRISPR complex, including the guide sequence to be tested, may be provided to a host cell having the corresponding target sequence, such as by transfection with vectors encoding the components of the CRISPR sequence, followed by an assessment of preferential cleavage within the target sequence. Similarly, cleavage of a target polynucleotide sequence may be evaluated in a test tube by providing the target sequence, components of a CRISPR complex, including the guide sequence to be tested and a control guide sequence different from the test guide sequence, and comparing binding or rate of cleavage at the target sequence between the test and control guide sequence reactions. Other assays are possible, and will occur to those skilled in the art.

As used herein, "guide RNA" generally refers to RNAs that guide the insertion or deletion of uridine residues into mitochondrial mRNAs in kinetoplastid protists in a process known as RNA editing. The terms "guide RNA" and "gRNA" are also used in prokaryotic DNA editing involving CRISPR and Cas9. For this prokaryotic DNA-editing system, the gRNA confers target sequence specificity to the CRISPR-Cas9 system. These gRNAs are non-coding short RNA sequences which bind to the complementary target DNA sequences. Guide RNA binds to the Cas9 enzyme and the gRNA sequence guides the complex via pairing to a specific location on the DNA, where Cas9 performs its endonuclease activity by cutting the target DNA strand. By inhibiting or removing endonuclease activity, a Cas9 protein can be engineered to bind a target nucleic acid in the presence of a complementary gRNA, as described further herein.

In addition to expression of the Cas9 nuclease, the CRISPR-Cas9 system can include a specific RNA molecule to recruit and direct the nuclease activity to the region of interest. These guide RNAs take one of two forms: (1) a synthetic trans-activating CRISPR RNA (tracrRNA) plus a synthetic CRISPR RNA (crRNA) designed to cleave the gene target site of interest and (2) a synthetic or expressed single guide RNA (sgRNA) that consists of both the crRNA and tracrRNA as a single construct. The crRNA and the tracrRNA form a complex which acts as the guide RNA for the Cas9 enzyme. The sgRNA can be synthetically generated or made in vitro or in vivo from a DNA template.

As used herein, an "isolated" biological component (e.g., such as a nucleic acid molecule, protein, or cell) has been substantially separated or purified away from other biological components in the cell of the organism, or the organism itself, in which the component naturally occurs, such as other chromosomal and extra-chromosomal DNA and RNA, proteins and cells. Nucleic acid molecules and proteins that have been "isolated" may be understood to have been purified by standard purification methods. The term also embraces nucleic acid molecules and proteins prepared by recombinant expression in a host cell as well as chemically synthesized nucleic acid molecules and proteins.

As used herein, a "label" generally refers to an agent capable of detection, for example by ELISA, spectrophotometry, flow cytometry, or microscopy. For example, a label can be attached to a nucleic acid molecule or protein (indirectly or directly), thereby permitting detection of the nucleic acid molecule or protein. Examples of labels include, but are not limited to, radioactive isotopes, enzyme substrates, co-factors, ligands, chemiluminescent agents, fluorophores, haptens, enzymes, and combinations thereof.

Methods for labeling and guidance in the choice of labels appropriate for various purposes are discussed for example in Sambrook et al. (Molecular Cloning: A Laboratory Manual, Cold Spring Harbor, New York, 1989) and Ausubel et al. (In Current Protocols in Molecular Biology, John Wiley & Sons, New York, 1998).

As used herein, the term "linker" or "linked" means joined together, either directly or indirectly. For example, a first moiety may be covalently or noncovalently (e.g., electrostatically) linked to a second moiety. This includes, but is not limited to, covalently bonding one molecule to another molecule, noncovalently bonding one molecule to another (e.g., electrostatically bonding), non-covalently bonding one molecule to another molecule by hydrogen bonding, non-covalently bonding one molecule to another molecule by van der Waals forces, and any and all combinations of such couplings. Indirect attachment is possible, such as by using a "linker" (a molecule or group of atoms positioned between two moieties). In several embodiments, linked components are associated in a chemical or physical manner so that the components are not freely dispersible from one another. For example, two components may be covalently bound to one another so that the two components are incapable of separately dispersing or diffusing.

As used herein, the terms "non-naturally occurring" and "engineered" interchangeably indicate the involvement of the hand of man. These terms, when referring to nucleic acid molecules or polypeptides, generally indicate that the nucleic acid molecule or the polypeptide is at least substantially free from at least one other component with which they are naturally associated in nature and as found in nature.

As used herein, "nucleic acid" generally refers to a deoxyribonucleotide or ribonucleotide polymer, which can include analogues of natural nucleotides that hybridize to nucleic acid molecules in a manner similar to naturally occurring nucleotides. In one example, a nucleic acid molecule is a single stranded (ss) DNA or RNA molecule, such as a probe or primer. In another example, a nucleic acid molecule is a double stranded (ds) nucleic acid. In another example, a nucleic acid is a modified DNA or RNA molecule, such as a xenonucleic acid (XNA). In all such embodiments, these nucleic acids can be a target nucleic acid, as described further herein.

As used herein, "polypeptide," "peptide," and "protein" generally refer to a polymer in which the monomers are amino acid residues that are joined together through amide bonds. When the amino acids are alpha-amino acids, either the L-optical isomer or the D-optical isomer can be used, the L-isomers being preferred in nature. The term polypeptide is specifically intended to cover naturally occurring proteins, as well as those that are recombinantly or synthetically produced. A substantially purified polypeptide as used herein refers to a polypeptide that is substantially free of other proteins, lipids, carbohydrates or other materials with which it is naturally associated. In one embodiment, the polypeptide is at least 50%, for example at least 80% free of other proteins, lipids, carbohydrates or other materials with which it is naturally associated. In another embodiment, the polypeptide is at least 90% free of other proteins, lipids, carbohydrates or other materials with which it is naturally associated. In yet another embodiment, the polypeptide is at least 95% free of other proteins, lipids, carbohydrates or other materials with which it is naturally associated.

Conservative amino acid substitution tables providing functionally similar amino acids are well known to one of ordinary skill in the art. The following six groups are examples of amino acids that are considered to be conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W).

A non-conservative amino acid substitution can result from changes in: (a) the structure of the amino acid backbone in the area of the substitution; (b) the charge or hydrophobicity of the amino acid; or (c) the bulk of an amino acid side chain. Substitutions generally expected to produce the greatest changes in protein properties are those in which: (a) a hydrophilic residue is substituted for (or by) a hydrophobic residue; (b) a proline is substituted for (or by) any other residue; (c) a residue having a bulky side chain, e.g., phenylalanine, is substituted for (or by) one not having a side chain, e.g., glycine; or (d) a residue having an electropositive side chain, e.g., lysyl, arginyl, or histadyl, is substituted for (or by) an electronegative residue, e.g., glutamyl or aspartyl. Variant amino acid sequences may, for example, be 80, 90 or even 95 or 98% identical to the native amino acid sequence. Programs and algorithms for determining percentage identity can be found at the NCBI website.

As used herein, "probe" generally refers to a short sequence of nucleotides, such as at least 8, at least 10, at least 15, at least 20, or at least 21 nucleotides in length, which can be used to detect the presence of a complementary sequence by molecular hybridization. In particular examples, oligonucleotide probes include a label that permits detection of oligonucleotide probe:target sequence hybridization complexes. Laboratory standards and values can be set based on a known or determined population value and can be supplied in the format of a graph or table that permits comparison of measured, experimentally determined values.

As used herein, the term "purified" does not require absolute purity; rather, it is intended as a relative term. Thus, for example, a purified protein preparation is one in which the protein referred to is more pure than the protein in its natural environment within a cell. For example, a preparation of a protein is purified such that the protein represents at least 50% of the total protein content of the preparation. Similarly, a purified oligonucleotide preparation is one in which the oligonucleotide is purer than in an environment including a complex mixture of oligonucleotides. Purity of a compound may be determined, for example, by high performance liquid chromatography (HPLC) or other conventional methods.

As used herein, "recombinant" generally refers to recombinant nucleic acid or protein that has a sequence that is not naturally occurring or has a sequence that is made by an artificial combination of two otherwise separated segments of sequence. This artificial combination is often accomplished by chemical synthesis or by the artificial manipulation of isolated segments of nucleic acids, for example, by genetic engineering techniques. The term recombinant includes nucleic acids and proteins that have been altered solely by addition, substitution, or deletion of a portion of a natural nucleic acid molecule or protein.

As used herein, the term "subject" includes human and non-human animals. "Patient" and "subject" are used interchangeably herein.

As used herein, the terms, "substantial identity" or "substantially identical" generally refer to a nucleic acid or fragment thereof, that, when optimally aligned with appropriate nucleotide insertions or deletions with another nucleic acid (or its complementary strand), refers to a nucleotide sequence having at least about 95% sequence identity, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutant thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

As used herein, "variant" generally refers to a peptide or polypeptide that differs in amino acid sequence by the insertion, deletion, or conservative substitution of amino acids, but retain at least one biological activity. "SNP" refers to a variant that is a single nucleotide polymorphism. Representative examples of "biological activity" include the ability to be bound by a specific antibody or to promote an immune response. Variant is also used herein to describe a protein with an amino acid sequence that is substantially identical to a referenced protein with an amino acid sequence that retains at least one biological activity. A conservative substitution of an amino acid, i.e. replacing an amino acid with a different amino acid of similar properties (e.g., hydrophilicity, degree, and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. Substitution of amino acids having similar hydrophilicity values can result in peptides retaining biological activity, for example immunogenicity, as is understood in the art. Substitutions may be performed with amino acids having hydrophilicity values within ±2 of each other. Both the hydrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

As used herein, "treat," "treating" or "treatment" are each used interchangeably to describe reversing, alleviating, or inhibiting the progress of a disease and/or injury, or one or more symptoms of such disease, to which such term applies. Depending on the condition of the subject, the term also refers to preventing a disease, and includes preventing the onset of a disease, or preventing the symptoms associated with a disease. A treatment may be either performed in an acute or chronic way. The term also refers to reducing the severity of a disease or symptoms associated with such disease prior to affliction with the disease. Such prevention or reduction of the severity of a disease prior to affliction refers to administration of a pharmaceutical composition to a subject that is not at the time of administration afflicted with the disease. "Preventing" also refers to preventing the recurrence of a disease or of one or more symptoms associated with such disease. "Treatment" and "therapeutically," refer to the act of treating, as "treating" is defined above.

2. Bioelectronic Devices and Systems

Embodiments of the present disclosure provides devices, systems, and methods related to single molecule detection.

In particular, the present disclosure provides devices and methods for sequence-specific detection of a nucleic acid target using current fluctuations as a readout for protein binding to the nucleic acid target. As described herein, certain aspects of the bioelectronic devices and method can be used to detect and identify any nucleic acid target for the purpose of diagnosis and/or treatment.

Figure 2:
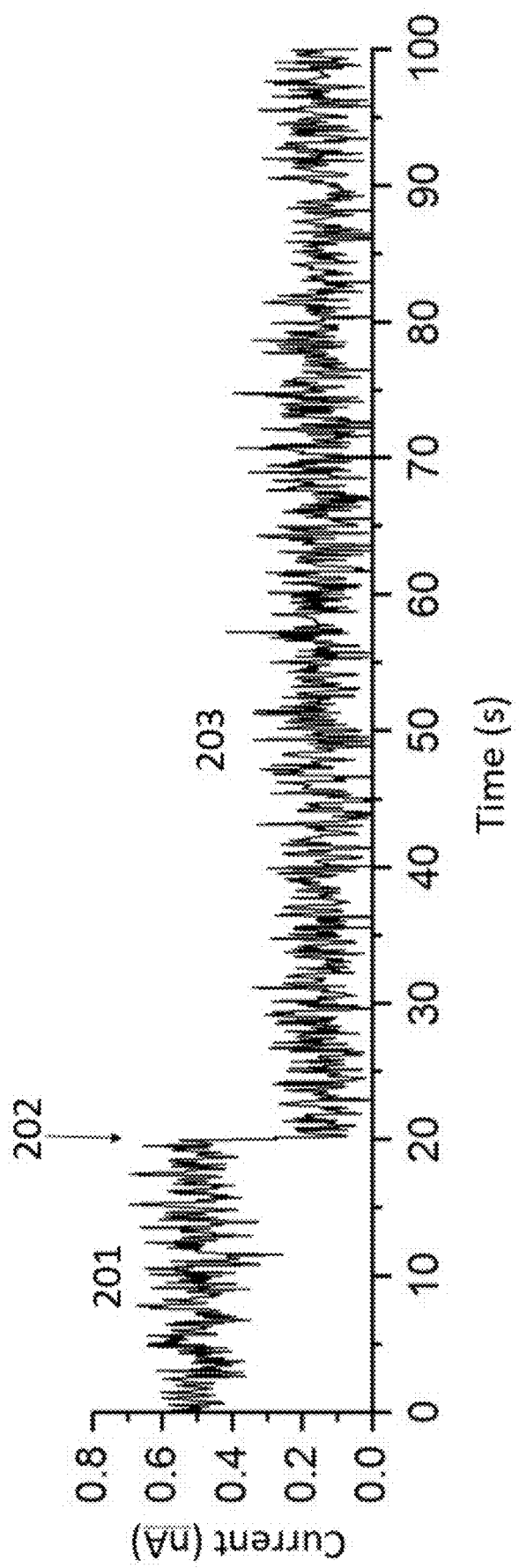
FIG. 2: Representative graph of an electrical signal generated when a target DNA sequence binds a CRISPR-associated protein in the presence of a corresponding guide RNA, according to one embodiment of the present disclosure.

In accordance with these embodiments, the devices of the present disclosure include a device for single-molecule electronic sequence detection. In some embodiments, the device comprises a first electrode, a second electrode, and a CRISPR-associated protein functionally coupled to the first electrode and second electrode, such as by chemical modification of the CRISPR-associated protein. This allows an electrical current to pass from the first electrode to the second electrode via the CRISPR-associated protein, such that when the CRISPR-associated protein binds a target nucleic acid in the presence of a corresponding guide RNA, a signal is detected based on the fluctuation of the current that indicates that the target nucleic acid is present (FIG. 2).

Embodiments of the present disclosure also include a system that includes a plurality of CRISPR-associated proteins, with each CRISPR-associated protein connected to a pair of electrodes. In accordance with these embodiments, introducing a unique guide RNA to a plurality of sites on the pair of electrodes, such as exposing the device to a solution (e.g., sample from a subject) containing a plurality of targets, leads to each CRISPR-associated protein in the device to form a complex with the guide RNA and the target nucleic acid that can be measured as a characteristic fluctuation in current (e.g., decrease in current).

Also disclosed are various embodiments of a method of detecting binding of a single target nucleic acid molecule. In accordance with these embodiments, the method includes combining a bioelectronic device comprising a CRISPR-associated protein with a guide RNA and a corresponding target nucleic acid, applying a voltage bias between the first and the second electrode (e.g., 100 mV or less), and detecting a shift in current (e.g., a decrease in current) upon formation of the complex comprising the CRISPR-associated protein, the guide RNA, and the corresponding target nucleic acid. In some embodiments, the method includes recording the current through the CRISPR-associated protein and detecting a change in current when the CRISPR-associated protein binds the target DNA or RNA corresponding to the target complementary sequence of the guide RNA.

Referring to FIG. 1, embodiments of the present disclosure include an exemplary bioelectronic device comprising a Cas protein 101 programmed by single guide RNA (sgRNA) 102. The target sequence region of the sgRNA is shown bound to a captured double-stranded DNA, 103 complementary to the target RNA sequence and containing the protospacer adjacent motif (PAM) sequence (NGG for many Cas proteins) 104 on the opposite strand 105 of the DNA. The Cas protein 101 is chemically modified at a plurality of sites such as two sites on the protein surface, 106 and 107, so as to form chemical bonds with linker molecules 108 and 109. The linker molecules, 108 and 109 are in turn attached by chemical bonds 110 and 111 to two metal electrodes, 112 and 113. A voltage (V) 114 is applied across the electrodes and a current (I) 115 is recorded. As described further below, the Cas protein changes its electrical conductivity significantly, such as by about 50 to about 300 percent, including, but not limited to, 50%, 60%, 65%, 70%, 75%, 80%, 85%, 90%, 95%, 100%, 110%, 120%, 130%, 140%, 150%, 160%, 170%, 180%, 190%, 200%, 210%, 220%, 230%, 240%, 250%, 260%, 270%, 280%, 290% and 300% percent when it binds a target DNA sequence.

In some embodiments, a Cas protein is rendered nuclease deficient, such as by one or more mutations, which produces a dCas protein. For example, the resulting dCas protein can remain in a conformation adopted when the target sequence is first trapped, with the result that the current passing through the Cas protein remains at a new, and generally higher level, such as at least a 2-fold, 3-fold, 5-fold or more increase after finding the target DNA sequence.

An example of the type of signal to be expected from the device of FIG. 1 is provided in FIG. 2. For example, when a bias of 50 mV for the case where the molecular conductance in the absence of target DNA, or in the presence of DNA not containing the target sequence is about 10 nS, a current of about 0.5 nA 201 is observed. After introduction and binding of the target DNA, the conductance in this case decreases to about 3 nS corresponding to a current of about 0.15 nA 202, where it remains stable at that value 203 for the case of a nuclease deficient dCas protein that remains stably bound to the target. FIG. 2 is a representative example and is not meant to be limiting. The bioelectronic devices of the present disclosure can detect a range of conductance changes on binding a target molecule, as discussed further below.

When a bias above 100 mV is applied, noise is typically generated at the contacts to the proteins. Therefore, in order to detect changes associated with changes of the conformation of the protein with an optimal signal to noise, an applied bias of about 100 mV or less is used. For example, an applied bias of about 5 mV, about 10 mV, about 15 mV, about 20 mV, about 25 mV, about 30 mV, about 35 mV, about 40 mV, about 45 mV, about 50 mV, about 55 mV, about 60 mV, about 65 mV, about 70 mV, about 75 mV, about 80 mV, about 85 mV, about 90 mV, about 95 mV, about 100 mV can be used, including any range or subrange of values.

An example of the chemical steps required to wire a nuclease-deficient dCas9 protein is given below, but it is contemplated that any protein in the CRISPR-associated family can be used with the bioelectronic devices of the present disclosure. Examples, in addition to Cas9, include but are not limited to, Cas1, Cas2, Cas3, Cas4, Cas5, Cas6, Cas7, Cas8, Cas10, Cas12, Cas13, Cas14, and their nuclease-deficient dCas equivalents. Exemplary Cas proteins are disclosed in Marakova et al. (*Nature reviews. Microbiology*, 2015. 13(11): p. 722-736), which is hereby incorporated by reference in its entirety.

In some embodiments, an RNA targeting CRISPR protein for Type III-A CRISPR-Cas Csm Complex of *Thermus thermophilus* (Staals et al., *Molecular Cell*, 2014. 56(4): p. 518-530) is used with the bioelectronic devices disclosed herein, thus allowing for the identification of RNA targets without the need of reverse transcriptase. This capability of the device is advantageous for the detection of viral RNA genomes and sequences. In some embodiments, the bioelectronic devices of the present disclosure can be used for direct single-molecule detection of the genomic components of viruses, such as coronaviruses, e.g., severe acute respiratory syndrome (SARS), Middle East respiratory syndrome (MERS), and/or SARS-Cov2 (see, e.g., FIGS. 7A-7B).

Figure 3A:
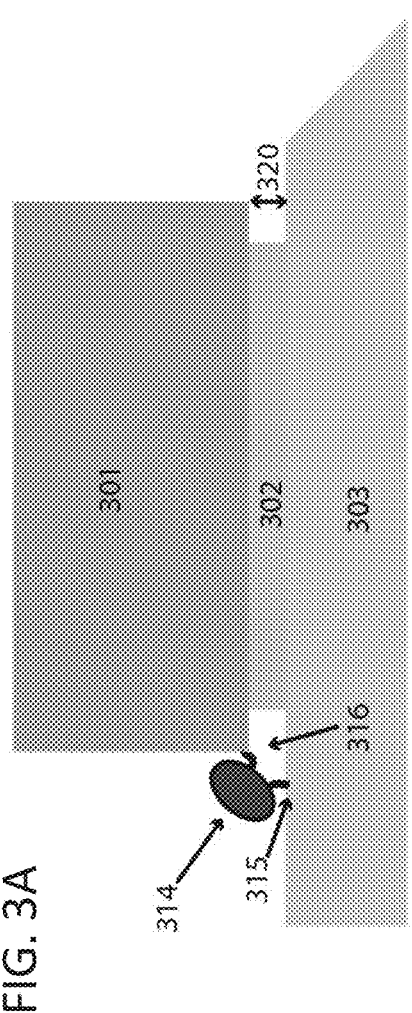
FIGS. 3A-3B: Representative schematic diagram of a single CRISPR-associated protein (e.g., Cas9) mounted between electrodes via two specific chemical contacts (FIG. 3A), and mounted between electrodes with one specific chemical contact and one non-specific physical contact (FIG. 3B), according to embodiments of the present disclosure.
Figure 3B:
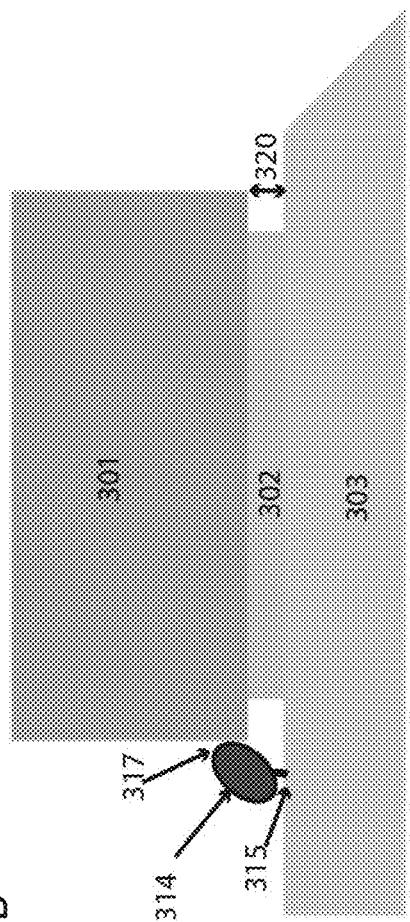

FIGS. 3A-3B include embodiments of the device of FIG. 1. Here, a top electrode 301 is separated from a bottom electrode 303 by a thin layer of dielectric 302. This device is fabricated as disclosed in U.S. Provisional Patent Application No. 62/975,748, filed Feb. 12, 2020, and corresponding PCT Application No. PCT/US21/17583, filed Feb. 11, 2021, both of which are hereby incorporated by reference in their entireties and for all purposes. The various configurations and geometries of the bioelectronic devices of the present disclosure can include any aspects of the devices disclosed in U.S. Pat. No. 10,422,787 and PCT Appln. No. PCT/US2019/032707, both of which are herein incorporated by reference in their entirety and for all purposes.

Briefly, in some embodiments, the first and second electrodes are formed out of a combination of metals. For example, an exemplary electrode can be fabricated by depositing a dielectric on an electrode, such as a gold electrode. The substrate may be any dielectric material such as glass, fused silica, or quartz. The dielectric substrate may be a layer of dielectric insulation. Alternately, the substrate can be a high-resistivity silicon with a thick (about 500 nm) layer of oxide grown on it. For example, the oxide layer may be between about 400 nm to about 600 nm, including about 400 nm, about 450 nm, about 500, about 550 nm or about 600 nm thick. The gold electrode may be patterned according to methods known in the art, such as by standard lift-off methods. If a dual layer of photoresist is used so as to allow for an undercut mask, the edges of the gold electrode can be free of fencing asperities. In some embodiments, if the gold is deposited at an angle onto a rotating substrate with an undercut photoresist mask, the edges can be made to be gently sloping. The electrode can be from about 50 nm to about 10 microns wide and from about 5 nm to about 1 micron thick. Dielectric material can be deposited over one end of the gold electrode using standard photolithographic methods followed by atomic layer deposition (ALD). This dielectric may be $SiO_2$, $HfO_2$, $Al_2O_3$ or any other dielectric material that can be reliably deposited as a thin film using atomic layer deposition. Typically, the amount of dielectric deposited is from about 1 nm to about 50 nm. In some embodiments, ALD growth of very thin films can be obtained by treating the surface of the first electrode (e.g., a planar electrode, a bottom electrode) with a very thin (about 1 nm or less) layer of a reactive metal such as Cr, Ti or Al. In some embodiments, the dielectric layer is deposited in the gap between electrodes; however, in other embodiments, a dielectric between this gap is not required.

A second electrode can be deposited so as to lie over the top of (e.g., be parallel to) dielectric-coated first electrode. The second electrode can be any noble metal. In some embodiments, the second electrode is made from platinum or palladium. The second electrode may be from about 50 nm to about 10 microns in width and from about 5 nm to about 100 nm thick. In determining the width of the second electrode, the constraint is that the edges of the second electrode lie over a planar portion of the first electrode.

In an additional step, the dielectric can be etched away from the first electrode using a slow, wet-etchant, such as buffered HF (typically a solution of HF and $NH_4F$), piranha solution ($H_2SO_4$ and $H_2O_2$) and/or a $HCl/H_2O_2$ solution for $HfO_2$ dielectric layers and $SiO_2$, and Tetramethylammonium hydroxide (TMAH) or a similar base like KOH for $Al_2O_3$ dielectric layers. The amphoteric nature of the last atomic layer of oxide deposition can result is resistance to basic etches, and an added acids wash improves completeness of the layer removal. The result is a slight undercutting of the dielectric under the junction.

The covering of the edge of the gold electrode with dielectric can prevent or reduce motion of the edge atoms of the gold electrode. By using a more stable metal (e.g., Pd, Pt) for the second electrode, the edge of the second electrode defines a sharp junction with respect to the underlying planar gold surface. Another important aspect is the avoidance of RIE or other particle-bombardment methods to expose a junction as used in some earlier designs of layered junction devices.

In some embodiments, it may be desirable to incorporate further protection at the edge of the first gold electrode. In an additional step, a second layer of dielectric can be patterned over the edges of the first gold electrode.

In some embodiments, the entire device may be passivated using, for example, a layer of SU8 polymer of about 500 nm to about 15 microns thickness, opened to expose the junction in a small window of a few microns on each side. An alternative is from about 50 nm to about 500 nm thick layer of $HfO_2$, $Al_2O_3$, $SiN_x$, or $SiO_2$, preferably deposited by atomic layer deposition. In some embodiments, the thickness of the layer is from about 50 nm to about 400 nm. In some embodiments, the thickness of the layer is from about 50 nm to about 300 nm. In some embodiments, the thickness of the layer is from about 50 nm to about 200 nm. In some embodiments, the thickness of the layer is from about 50 nm to about 100 nm. In some embodiments, the thickness of the layer is from about 100 nm to about 500 nm. In some embodiments, the thickness of the layer is from about 200 nm to about 500 nm. In some embodiments, the thickness of the layer is from about 300 nm to about 500 nm. In some embodiments, the thickness of the layer is from about 500 nm to about 500 nm. In some embodiments, the thickness of the layer is from about 100 nm to about 400 nm. In some embodiments, the thickness of the layer is from about 100 nm to about 300 nm. In some embodiments, the thickness of the layer is from about 200 nm to about 400 nm.

Once the window is opened, the molecular junction may be further cleaned by exposure to an oxygen plasma, UV ozone, or other plasma species, and functionalized with molecules as described in Zhang et al. (referenced above), which is hereby incorporated by reference. The second electrode and first electrode can each be functionalized. In some embodiments, the Cas protein 314 is attached to the top electrode 301 via the linker 316 (see FIGS. 3A-3B; the equivalent of 108 in FIG. 1) and to the bottom electrode via the linker 315 (see FIGS. 3A-3B; the equivalent of 109 in FIG. 1). In the case where the linkers are direct, short covalent bonds between the protein and the electrode, the gap between the electrodes 320 could be as small as 1 nm. In the event that the linker molecule is streptavidin (as described below) the gap can be from about 2 to about 8 nm. In the event that a fibrous protein is used as the linker, the gap could be from about 5 nm to about 50 nm.

In many circumstances signals are also obtained when only one specific chemical contact is made to one of the electrodes, the second contact 317 being made by physical, non-specific contact with the second electrode. This is illustrated in FIG. 3B where the specific contact 315 is shown made to the bottom electrodes, with the second, non-specific contact made to the top electrode.

It will be recognized by one of ordinary skill in the art based on the present disclosure that since the work function of metal alloys is generally given by a weighted average of the work functions of their component metals, gold alloys may be substituted for the first electrode. For example, white gold (e.g., alloys with palladium and or silver) and other gold alloys such as with copper or nickel may be used in place of pure gold. Generally, any noble metal alloy can be used for fabrication of either the first and/or second electrode, including but not limited to alloys such as palladium-platinum, palladium-silver, platinum-silver and others.

In some embodiments, a modified Cas protein, such as dCas9, is used with the disclosed device and methods. In some embodiments, dCas9 is a double point-mutant Cas9 from *S. pyogenes* that retains programmable functionality but lacks nuclease activity. The mutations are D10A and H840A and are located in the RuvC and HNH nuclease domains, respectively. Electrical connections were made by inserting the avitag biotinylatable sequence at two points on the dCas9. In this embodiment, avitag sequences were inserted at the N and C termini, the terminal sequences being: N-terminal sequence: MGSSHHHHHHSSGLVPRGSH-MASMTGGQQMGRGSEFELRRQACGRMGL NDIFEA-QKIEWHEA (SEQ ID NO: 1) and C-terminal sequence: VGLNDIFEAQKIEWHEAGGSGGGLEHHHHHH (SEQ ID NO: 2). In these sequences, the avitag peptide is shown in italics with the biotinylatable lysine in bold. In some embodiments, a His tag is inserted at both N and C terminal regions for protein purification. These avitags are biotinylated using the BirA enzyme. These biotins then form the chemical links shown as 106 and 107 in FIG. 1 and complex with streptavidin molecules which are used as the linkers 108 and 109 in FIG. 1. Electrodes are functionalized with thiolated biotin molecules, forming the second chemical bond labeled as 110 and 111 in FIG. 1.

Figure 4:
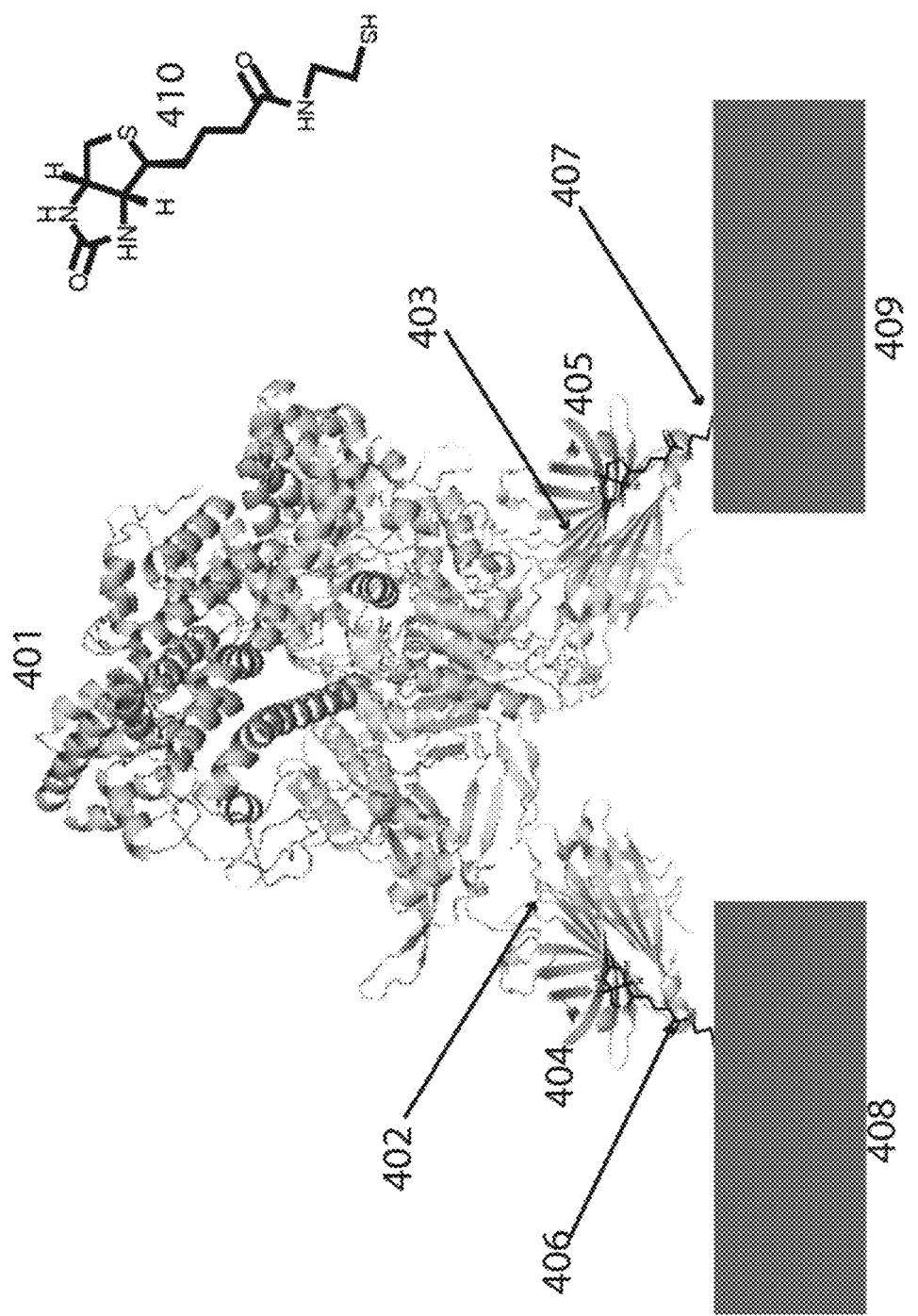
FIG. 4: Representative schematic diagram of a CRISPR-associated protein (e.g., dCas9) functionally coupled to streptavidin linker molecules via biotin-streptavidin bonds, according to one embodiment of the present disclosure.

The assembled molecular device is shown in FIG. 4. The dCas9 protein 401 biotinylated at the N- and C-termini 402, 403 is bound to streptavidin molecules 404, 405 via biotin-streptavidin bond. Electrodes, 408, 409 functionalized with thiolated biotin 406, 407 are bonded to the streptavidin molecules 404, 405 by means of biotin-streptavidin bonds. The structure of the thiolated biotin molecule is shown in detail by 410 in FIG. 4.

In some embodiments, a Halo-Tag peptide sequence can be incorporated into the N- and C-termini of the dCas9. The Halo-Tag peptide sequence is provided as follows: MHHHHHHGGGGSGGGGSGGGGSMAEIGTGFPFD-PHYVEVLGERMHYVDVGPRDG TPVLFLHGNPTSSYVWRNIIPHVAPTHRCIAP-DLIGMGKSDKPDLGYFFDDHVRFMD AFIEAL-GLEEVVLVIHDWGSALGFHWAKRNPERVKGIAFME-FIRPIPTWDEWPEFAR ETFQAFRTTDVGRKLIIDQNVFIEGTLPMGVVRPLTE-VEMDHYREPFLNPVDREPLW RFPNELPIAGEPANI-VALVEEYMDWLHQSPVPKLLFWGTPGVLIP-PAEAARLAKSLPN CKAVDIGPGLNLLQEDNPDLIGSEIARWLSTLEIS-GDKKYSIGLAIGTNSVGWAVITDE YKVPSKKFKVLGNTDRHSIKKNLIGALLFDSGETAE-ATRLKRTARRRYTRRKNRICY LQEIFSNE-MAKVDDSFFHRLEESFLVEEDKKHERH-PIFGNIVDEVAYHEKYPTIYHLR KKLVDSTDKADLRLIYLALAH-MIKFRGHFLIEGDLNPDNSDVDKLFIQLVQTYNQLF EENPINASGVDAKAILSARLSKSRRLENLIAQLPGEK-KNGLFGNLIALSLGLTPNFKSN FDLAEDAKLQLSKD-TYDDDLDNLLAQIGDQYADLFLAAKNLSDAI-LLSDILRVNTEIT KAPLSASMIKRYDEHHQDLTLLKALVRQQLPEKYKE-IFFDQSKNGYAGYIDGGASQE EFYKFIKPILEKMDG-TEELLVKLNREDLLRKQRTFDNGSIPHQIHLGEL-HAILRRQEDF YPFLKDNREKIEKILTFRIPYYVGPLARGNSR-FAWMTRKSEETITPWNFEEVVDKGAS AQSFIER-MTNFDKNLPNEKVLPKHSLLY-EYFTVYNELTKVKYVTEGMRKPAFLSGEQ KKAIVDLLFKTNRKVTVKQLKEDYFKKIECFDS-VEISGVEDRFNASLGTYHDLLKIIK DKDFLD-NEENEDILEDIVLTLTLFEDREMIEERLKTYAHL-FDDKVMKQLKRRRYTGW GRLSRKLINGIRDKQSGKTILDFLKSDGFANRNFMQ-LIHDDSLTFKEDIQKAQVSGQG DSLHEHIANLAG-SPAIKKGILQTVKVVDELVKVMGRHKPENIVI-EMARENQTTQKGQ KNSRERMKRIEEGIKELGSQILKEHPVENTQLQNEK-LYLYYLQNGRDMYVDQELDIN RLSDYDV-DAIVPQSFLKDDSIDNKVLTRSDKNRGKSDNVP-SEEVVKKMKNYWRQLL NAKLITQRKFDNLTKAERGGLSELDKAGFIKRQLVE-TRQITKHVAQILDSRMNTKYD ENDKLIREVKVITLK-SKLVSDFRKDFQFYKVREINNYHHAHDAYL-NAVVGTALIKKY PKLESEFVYGDYKVYDVRKMIAKSEQEIGKAT-AKYFFYSNIMNFFKTEITLANGEIRK RPLIETNGET-GEIVWDKGRDFATVRKVLSMPQVNIVKKTE-VQTGGFSKESILPKRNSD KLIARKKDWDPKKYGGFDSPTVAYSVLV-VAKVEKGKSKKLKSVKELLGITIMERSSF EKNPID-FLEAKGYKEVKKDLIIKLPKYSLFELENGRKRMLA-SAGELQKGNELALPSK YVNFLYLASHYEKLKGSPEDNEQKQLFVEQHKHYL-DEIIEQISEFSKRVILADANLDK VLSAYNKHRDK-PIREQAENIIHLFTLTNLGAPAAFKYFDTTIDRKRYT-STKEVLDATLI HQSITGLY-ETRIDLSQLGGDSRADPKKKRKVMAEIGTGFPFD-PHYVEVLGERMHYVD VGPRDGTPVLFLHGNPTSSYVWRNIIPHVAPTHR-CIAPDLIGMGKSDKPDLGYFFDDH VRFMDAFIEAL-GLEEVVLVIHDWGSALGFHWAKRNPERVKGIAFME-FIRPIPTWDEW PEFARETFQAFRTTDVGRKLI-IDQNVFIEGTLPMGVVRPLTEVEMDHYREP-FLNPVDR EPLWRFPNELPIAGEPANI-VALVEEYMDWLHQSPVPKLLFWGTPGVLIPPAEAAR-LA KSLPNCKAVDIGPGLNLLQEDNPDLIGSEIARWL-STLEISG (SEQ ID NO: 3). Halo-Tag is a 33 kDa mutagenized haloalkane dehalogenase that forms covalent attachments to substituted chloroalkane linker derivatives (Halo-Ligand). Similarly to the Streptavidin-biotin connection, the chloroalkane linker extends 1.4 nm into the hydrophobic core of Halo-Tag. Commercially available Halo-ligand derivatives include the invariant chloroalkane moiety followed by 4 ethylene glycol repeats, and a reactive sulfahydryl, succinimidyl ester, amine, or iodoacetamide group, among many other options.

In some embodiments, electrode surfaces are functionalized with Thiol-PEG4-Chloroalkane ligand (Halo-Tag Thiol O4 Ligand), positioned 4.5 nm apart, and capture dCas9/Cas13a with N & and C-terminal Halo-Tag fusions. In some embodiments, chemically-reactive amino acids are inserted at any chosen pair of sites on the Cas protein by repurposing stop codons to incorporate non-natural amino acids such as azido-alanine or azido lysine. These serve as attachment sites for biotinylated or thiolated chemical linkers.

In accordance with the above, embodiments of the present disclosure include a bioelectronic device for detecting a target nucleic acid. In some embodiments, the device includes a first electrode, a second electrode, and at least one CRISPR-associated protein. In some embodiments, the CRISPR-associated protein is chemically modified to form a chemical bond with at least one of the first and the second electrodes. In some embodiments, the chemical modification allows an electrical current to pass through the CRISPR-associated protein, and the binding of the CRISPR-associated protein to a target nucleic acid causes a shift in the current. In some embodiments, the CRISPR-associated protein is a Cas family member protein selected from the group consisting of Cas1, Cas2, Cas3, Cas4, Cas5, Cas6, Cas7, Cas8, Cas10, Cas12, Cas13, Cas14, their nuclease-deficient dCas equivalents, and any variants or derivatives thereof. In some embodiments, the CRISPR-associate protein is Cas9 protein or dCas9.

As described further herein, the ability of the bioelectronic systems and devices of the present disclosure to identify and/or detect a target nucleic acid depends at least in part on the specificity of a guide RNA for a given target nucleic acid (e.g., in a sample from a subject). The specificity of CRISPR-Cas systems is well known in the art; however, the bioelectronic systems and devices of the present disclosure harness the specificity of CRISPR-Cas systems to develop methods that enable rapid, sensitive and specific analyses of nucleic acid sequences, which positively affects precise disease diagnostics and effective clinical treatments by providing direct insight into clinically relevant genetic information. The bioelectronic systems and devices of the present disclosure repurpose CRISPR/Cas systems for diagnostic functions, thus providing a robust diagnostic platform with enhanced flexibility, sensitivity, and specificity for both clinical and for point-of-care settings.

For example, as described further herein, any RNA or DNA molecule (or derivative thereof) can be targeted for detection using the bioelectronic devices of the present disclosure. In some embodiments, a particular RNA or DNA target sequence (e.g., in a sample from a subject or from an environmental or industrial sample) can be identified and a corresponding guide RNA can be generated. Methods for identifying a guide RNA sequence for a given RNA or DNA target include but are not limited to, those disclosed in Li, B. et al., "CRISPR-SE: a brute force search engine for CRISPR design," *NAR Genomics and Bioinformatics*, Volume 3, Issue 1, March 2021 (lqab013), as well as any related guide RNA databases (e.g., http://renlab.sdsc.edu/CRISPR-SE/); Metsky, H. C. et al., "Diagnostic design with machine learning model-based optimization," bioRxiv 2020.11.28.401877 (doi: https://doi.org/10.1101/2020.11.28.401877); and Ackerman, C. M. et al., "Massively multiplexed nucleic acid detection with Cas13," *Nature* volume 582, pages 277-282(2020), all of which are herein incorporated by reference in their entireties.

To facilitate the generation of the bioelectronic devices and systems of the present disclosure, chemical modifications can be made to a CRISPR-associated protein, including adding a linker to facilitate attachment to one or more electrodes. In some embodiments, the chemical modification comprises adding at least two linkers on at least two sites on the CRISPR-associated protein, with the at least two linkers attached to each of the first and second electrodes. In some embodiments, one linker of the at least two linkers is attached to site on the CRISPR-associated protein, and another linker of the at least two linkers is attached to a different site on the CRISPR-associated protein.

In some embodiments, the linker is attached to an inactive region of the CRISPR-associated protein via a covalent chemical bond. In some embodiments, the chemical modification comprises biotinylating the CRISPR-associate protein. In some embodiments, the linker comprises thio-streptavidin. In some embodiments, the CRISPR-associate protein and the first and second electrodes are biotinylated, and the linker comprises a streptavidin molecule having at least two biotin binding sites. In some embodiments, the chemical modification comprises a Halo-Tag fusion protein and a chloroalkane linker.

Embodiments of the present disclosure also include a method of detecting a target nucleic acid using any of the bioelectronic devices and systems described herein. In accordance with these embodiments, the method includes combining a bioelectronic device with a CRISPR-associated protein with a target nucleic acid and a corresponding guide RNA. The manner by which a CRISPR-associated protein is introduced to and combined with a target nucleic acid and a corresponding guide RNA will vary depending on a variety of factors relating to the parameters of the system (e.g., singleplex or multiplex), the target being detected, and/or the type of CRISPR-associated protein being used in the bioelectronic device. For example, in some embodiments, a guide RNA can be incubated with a Cas protein initially, and then the Cas protein can be functionally coupled to the electrodes. In other embodiments, a guide RNA and corresponding target nucleic acid can be incubated initially, and then they can be introduced to a Cas protein that has already been functionally coupled to the electrodes. In still other embodiments, a guide RNA can be incubated with a Cas protein that is functionally coupled to the electrodes, and then a target nucleic acid can be introduced.

In accordance with these embodiments, the method also includes applying a voltage bias between the first and the second electrode that is 100 mV or less, as described further herein. The method also includes detecting a shift in current (e.g., increased or decreased current) upon formation of a complex comprising the CRISPR-associated protein, the guide RNA, and the target nucleic acid. The shift in current is indicative of the presence of the target nucleic acid (e.g., in a sample obtained from a subject). In some embodiments of the method, the shift in current comprises a decrease in current as compared to the current when the CRISPR-associated protein is not bound to the target nucleic acid. In some embodiments of the method, the shift in current comprises an increase in current as compared to the current when the CRISPR-associated protein is not bound to the target nucleic acid.

The bioelectronic devices and systems of the present disclosure can be used to detect a target nucleic acid in a variety of ways. For example, embodiments of the present disclosure can be used to detect a portion of a larger target nucleic acid target, to detect single nucleotide polymorphisms (SNPs) within a target nucleic acid (e.g., to genotype an organism such as a virus), to detect a splice junction and/or an alternatively spliced nucleic acid target (e.g., indicative of a disease condition), and any other genetic alterations. As would be readily apparent to one of ordinary skill in the art based on the present disclosure, target nucleic acids can be derived from and/or associated with a pathogenic organism and parasites, including but not limited to, viruses (influenza viruses, coronaviruses (e.g., SARS-CoV-2 detection), flavivurses, alphaviruses, parainfluenza viruses, hepatitis virus, etc.), bacteria (*Mycobacterium tuberculosis, streptococcus, salmonella, Yersinia pestis, Bacillus anthracis*, etc.) and fungi (*candida*, blastomycosis, aspergillosis, etc.). Target nucleic acids can also be associated with a disease state or condition, type of infection (e.g. bacterial or viral), or one or more physiological parameters in a subject. For example, target nucleic acids can be associated with cancer biomarkers (e.g., cancer-specific mutations from circulating tumor DNA), immune indicators (e.g., cytokine and procalcitonin expression), and/or treatment conditions (e.g., to assess whether a given treatment has had an effect in a subject).

In some embodiments of the method, the target nucleic acid is contained in or derived from a sample from a subject, such as a bodily sample. In some embodiments, the sample is a blood sample, a serum sample, a plasma sample, a saliva sample, a urine sample, a stool sample, a cerebral spinal fluid (CSF) sample, a mucosal sample (e.g., respiratory sample), a sweat sample, a tear sample, and an amniotic fluid sample.

As used herein, "sample," "test sample," and "biological sample" generally refer to a fluid sample containing or suspected of containing a target nucleic acid. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis. In a particular example, the source is a mammalian (e.g., human) bodily substance (e.g., bodily fluid, blood such as whole blood (including, for example, capillary blood, venous blood, etc.), serum, plasma, urine, stool, saliva, sweat, sputum, semen, mucus, lacrimal fluid, lymph fluid, amniotic fluid, interstitial fluid, lower respiratory specimens such as, but not limited to, sputum, endotracheal aspirate or bronchoalveolar lavage, cerebrospinal fluid, feces, tissue, organ, one or more dried blood spots, or the like). Tissues may include, but are not limited to oropharyngeal specimens, nasopharyngeal specimens, skeletal muscle tissue, liver tissue, lung tissue, kidney tissue, myocardial tissue, brain tissue, bone marrow, cervix tissue, skin, etc. The sample may be a liquid sample or a liquid extract of a solid sample. In certain cases, the source of the sample may be an organ or tissue, such as a biopsy sample, which may be solubilized by tissue disintegration/cell lysis. Additionally, the sample can be a nasopharyngeal or oropharyngeal sample obtained using one or more swabs that, once obtained, is placed in a sterile tube containing a virus transport media (VTM) or universal transport media (UTM), for testing. Various methods of isolating or separating a target nucleic acid from a sample from a patient are known in the art, and can be used in conjunction with the methods of the present disclosure (e.g., Sureni V Mullegama, Michael O Alberti, Cora Au, Yan Li, Traci Toy, Vanina Tomasian, Rena R Xian, "Nucleic Acid Extraction from Human Biological Samples," Methods Mol Biol. 2019; 1897:359-383. doi: 10.1007/978-1-4939-8935-5_30). Additionally, a "sample" can include an environmental sample or a sample derived from the environment, including but not limited to, industrial processing streams, biological laboratories, wastewater samples, surface samples (e.g. swabbing door handles, handrails), food processing samples, pharmaceutical samples (e.g., small molecule and biologics), and the like. In some embodiments, a target nucleic acid is derived from or associated with an engineered organism or engineered microorganism. In some embodiments, the methods include sampling a particular environment to detect an engineered organism or engineered microorganism.

The method of the present disclosure can involve the use of a wide range of volumes of a fluid sample to be analyzed using the bioelectronic devices and systems described herein. In a few exemplary embodiments, the sample volume may be about 0.5 nL, about 1 nL, about 3 nL, about 0.01 µL, about 0.1 µL, about 1 µL, about 5 µL, about 10 µL, about 100 µL, about 1 mL, about 5 mL, about 10 mL, or the like. In some cases, the volume of the fluid sample is between about 0.01 µL and about 10 mL, between about 0.01 µL and about 1 mL, between about 0.01 µL and about 100 µL, or between about 0.1 µL and about 10 µL. In some cases, the fluid sample may be diluted prior to use in an assay. For example, in embodiments where the source containing a target nucleic acid is a human body fluid (e.g., blood, serum), the fluid may be diluted with an appropriate solvent (e.g., a buffer such as PBS buffer). A fluid sample may be diluted about 1-fold, about 2-fold, about 3-fold, about 4-fold, about 5-fold, about 6-fold, about 10-fold, about 100-fold, or greater, prior to use. In other cases, the fluid sample is not diluted prior to use in an assay.

In some cases, the sample may undergo pre-analytical processing. Pre-analytical processing may offer additional functionality such as nonspecific protein removal and/or mixing functionality. General methods of pre-analytical processing may include the use of electrokinetic trapping, AC electrokinetics, surface acoustic waves, isotachophoresis, dielectrophoresis, electrophoresis, or other pre-concentration techniques known in the art. In some cases, the fluid sample may be concentrated prior to use in an assay. For example, in embodiments where the source containing a target nucleic acid is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use. In some embodiments, samples may undergo enrichment, such as syndrome based targeted enrichment and PCR-based target enrichment.

Figure 6:
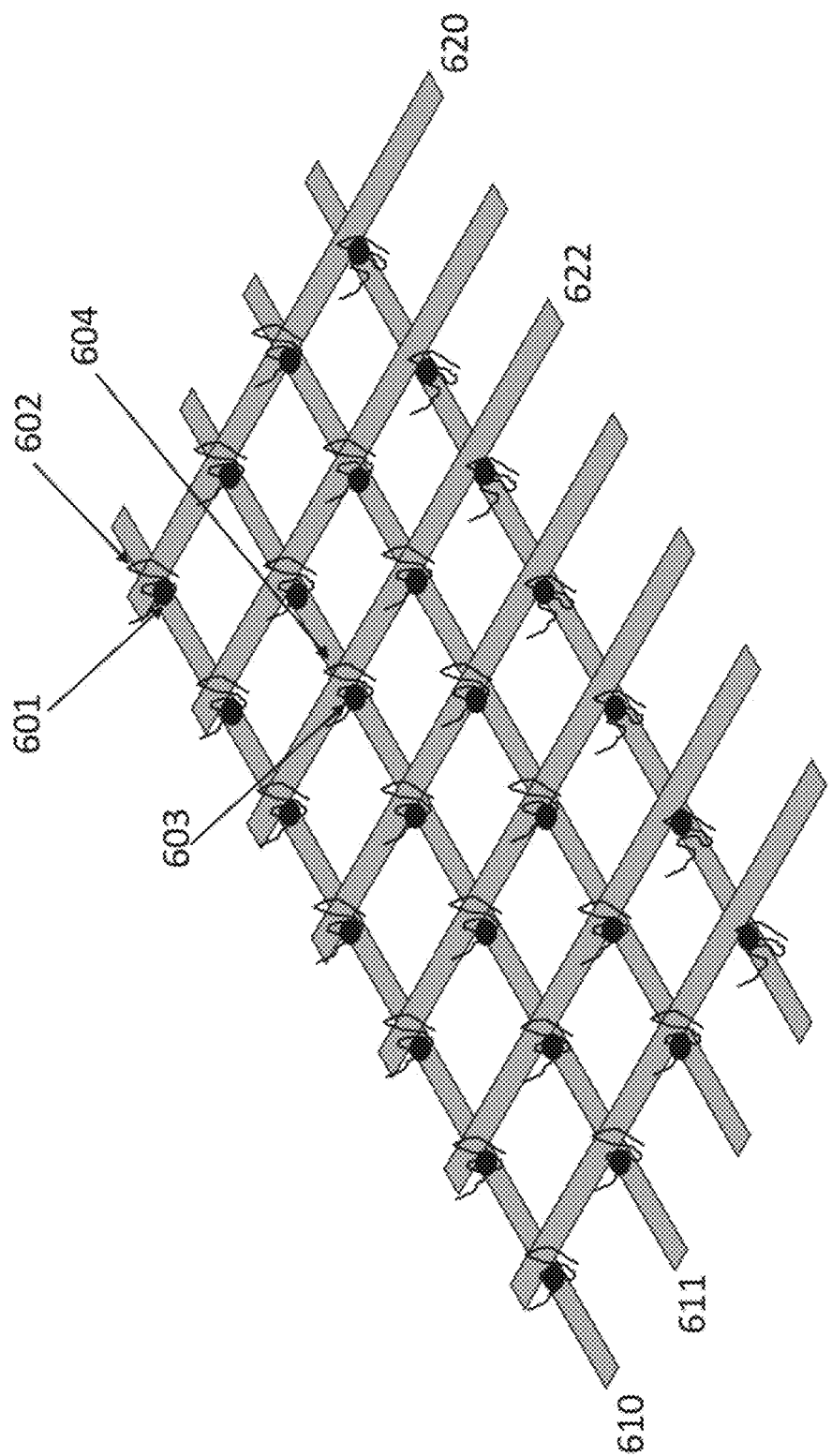
FIG. 6: Representative schematic diagram of an exemplary connection scheme (multiplexed platform), according to one embodiment of the present disclosure.

Embodiments of the present disclosure also include a system comprising a plurality of the bioelectronic devices described herein (FIG. 6). In some embodiments of the system, the plurality of bioelectronic devices are configured to detect more than one target nucleic acid based on corresponding guide RNA sequences. The ability to configure a plurality of the bioelectronic devices of the present disclosure into a multiplexed platform confers several advantages over currently available diagnostic platforms, including but not limited to direct and rapid single nucleic acid detection. Most, if not all, currently available methods rely on either indirect detection (e.g., collateral cleavage) or ensemble detection (e.g., graphene FET), which generally involve collateral cleavage to occur first to generate a signal, thus increasing detection times. Additionally, the multiplex systems of the present disclosure are "label free;" thus, they are not limited by the number of currently available fluorescent labels. In other words, a great number of targets (e.g., all ~265 known viruses) can be detected in a single assay platform because detection would not be limited by the availability of non-overlapping fluorophores that can be used simultaneously. Further, the multiplex systems of the present disclosure have digital quantification capability, whereas other currently available approaches can only correlate fluorescence intensity or total FET signal, both of which are not as precise.

In some aspects, the multiplex systems comprising a plurality of the bioelectronic devices of the present disclosure do not require continuous monitoring of proteins (e.g., CRISPR-associated proteins) as they detect their targets; they can be monitored periodically to assess binding of the CRISPR-associated protein to a target nucleic acid. This aspect is particularly useful because target detection depends on the time required for genetic material to diffuse to the protein and the time required for the CRISPR-associated protein to search the genetic material for the target. By having a number of CRISPR-associated proteins with the same guide sequences, for example, the multiplex systems of the present disclosure can rapidly decrease detection times. In accordance with these aspects, embodiments of the present disclosure include multiplex detection systems having multiple junctions with the same complexes so that the increase in signal from multiple junctions can be used for quantification of the target genetic material in the sample. In some embodiment, the location of the complexes on a chip detection platform can be optimized to maximize the detection signal strength, time to detection, and accuracy by accounting for the effects of diffusion (e.g., limiting the minimum diffusion length to increase detection time) and to circumvent accuracy potential challenges with non-specific amplification. In some embodiments, a single junction is functionalized with more than one CRISPR-associated protein all of which have an identical guide sequence.

The following examples are provided to illustrate particular features of certain embodiments. However, the particular features described below should not be construed as limitations on the scope of the disclosure, but rather as examples from which equivalents will be recognized by those of ordinary skill in the art. It will be recognized by one of ordinary skill in the art based on the present disclosure that any arrangement of two electrical connections by chemical means on any Cas protein will enable the device disclosed herein, such as presented in FIG. 1.

3. Examples

It will be readily apparent to those skilled in the art that other suitable modifications and adaptations of the methods of the present disclosure described herein are readily applicable and appreciable, and may be made using suitable equivalents without departing from the scope of the present disclosure or the aspects and embodiments disclosed herein. Having now described the present disclosure in detail, the same will be more clearly understood by reference to the following examples, which are merely intended only to illustrate some aspects and embodiments of the disclosure, and should not be viewed as limiting to the scope of the disclosure. The disclosures of all journal references, U.S. patents, and publications referred to herein are hereby incorporated by reference in their entireties.

The present disclosure has multiple aspects, illustrated by the following non-limiting examples.

Example 1

Guide RNA Sequences. As described further herein, the various embodiments of the bioelectronic devices and systems of the present disclosure can be used to identify or detect any nucleic acid target, owing at least in part to the specificity of the CRISPR-Cas systems known in the art. For example, guide RNA sequences were designed to detect target nucleic acids associated with virus, including but not limited to, SARS-CoV-2 and HPV16, as shown below in Table 1.

TABLE 1

Exemplary guide RNA sequences used to detect their corresponding target nucleic acids with the bioelectronic devices of the present disclosure.

| Target/SEQ ID NO | | sgRNA Sequence (5' to 3') | PAM |
|---|---|---|---|
| SARS-CoV-2 | Spike 1 (SEQ ID NO: 4) | ucuaaagccgaaaaacccugGUUUUAGAGCUAGAAAUAG CAAGUUAAAAUAAGGCUAGUCCG | AGG |
| | Spike 2 (SEQ ID NO: 5) | gcuacacuacgugcccgccgGUUUUAGAGCUAGAAAUAG CAAGUUAAAAUAAGGCUAGUCCG | AGG |
| | Matrix 1 (SEQ ID NO: 6) | uugcgcguacgcguuccaugGUUUUAGAGCUAGAAAUAG CAAGUUAAAAUAAGGCUAGUCCG | TGG |
| | Matrix 2 (SEQ ID NO: 7) | caauacgaagauguccacgaGUUUUAGAGCUAGAAAUAG CAAGUUAAAAUAAGGCUAGUCCG | AGG |
| | RdRp (SEQ ID NO: 8) | aguuguggcaucuccugaugGUUUUAGAGCUAGAAAUA GCAAGUUAAAAUAAGGCUAGUCCG | AGG |
| | Nucleocapsid (SEQ ID NO: 9) | gggcgcgaucaaaacaacguGUUUUAGAGCUAGAAAUAG CAAGUUAAAAUAAGGCUAGUCCG | CGG |
| HPV16 | L1 1 (SEQ ID NO: 10) | ccaccuauagggaacacugGUUUUAGAGCUAGAAAUAG CAAGUUAAAAUAAGGCUAGUCCG | GGG |
| | L1 2 (SEQ ID NO: 11) | uaaggaguaccuacgacaugGUUUUAGAGCUAGAAAUAG CAAGUUAAAAUAAGGCUAGUCCG | GGG |
| | E6 1 (SEQ ID NO: 12) | gcaacaguuacugcgacgugGUUUUAGAGCUAGAAAUAG CAAGUUAAAAUAAGGCUAGUCCG | AGG |
| Control | GFP 1 (SEQ ID NO: 13) | gagcuucagcuaccgcuacgGUUUUAGAGCUAGAAAUAG CAAGUUAAAAUAAGGCUAGUCCG | AGG |
| | dCas9 1 (SEQ ID NO: 14) | guacugauaaggcugacuugGUUUUAGAGCUAGAAAUAG CAAGUUAAAAUAAGGCUAGUCCG | CGG |

As shown in Table 1, the target complementary sequence is shown in small letters. The stem-loop regions and the GAAA tetraloop are shown in capitals. The PAM sequences are the required three nucleotides on the 3' end of the strand complementary to the recognition site, all having the generic sequence NGG for dCas9. Sequences were selected by finding unique sequences of the correct length for the Cas protein used (20 nucleotides for the dCa9 example given here) with the appropriate PAM sequence on the 3' side of the complementary recognition sequence on the double stranded DNA.

Example 2

Conductance changes on binding Target DNA. Experiments were conducted to determine the types of changes in conductance that occur when a CRISPR-associated protein and guide RNA bind a target DNA using the bioelectronic devices and systems of the present disclosure. For example, FIGS. 5A-5D include representative data obtained by programming dCas9 with the GFP1 targeting sequence (see Table 1; SEQ ID NO: 13). Conductances were measured by recording current-vs-voltage curves as described by the methods of Zhang et al. (Zhang, B., H. Deng, S. Mukherjee, W. Song, X. Wang, and S. Lindsay, *Engineering an Enzyme for Direct Electrical Monitoring of Activity*. ACS Nano, 2020, 14:1630-1638), which is hereby incorporated by reference in its entirety. FIG. 5A shows the distribution of conductances for a sgRNA programmed dCas9 in the absence of the target GFP sequence DNA. The low conductance peak at −0.5 (0.3 nS) 501 corresponds to singly connected molecules. The doubly connected molecules give a peak predominantly at about +1 (10 nS) 502. When the same collection of molecules was exposed to target DNA (FIG. 5B), the distribution of conductances changed. The peak owing to singly-connected molecules is still present 503, but moved to a lower conductance value. The peak owing to doubly-connected molecules 504 is greatly diminished. These distributions are stable on repeated measurement, likely corresponding to stable conformations of the dCas9. These changes are shown by superimposed distributions with (green points) and without (blue points) target DNA present in solution. The singly connected peak 501 moves to the lower value 503 on binding target DNA, and the doubly connected peak 502 almost disappears 504 on binding target DNA.

To demonstrate the specificity, these experiments were repeated using blue fluorescent protein (BFP) as an off-target DNA sequence. When an off-target DNA sequence was introduced to the sgRNA loaded dCas9 molecules, the distribution of conductance values 506 did not change (FIG. 5D). The binding of a target is indicated by a change in conductance, usually to a lower value. While the present example corresponds to the use of bioelectronic devices comprising dCas9, it will be recognized by one of ordinary skill in the art based on the present disclosure that this approach can be used to calibrate the changes in conductance for any Cas protein binding any DNA or RNA target.

Example 3

Systems and device arrays. Embodiments of the present disclosure also include bioelectronic systems (e.g., device arrays or multiplexed devices) that have the capability of detecting a plurality of DNA and/or RNA targets within a single sample. Exemplary configurations of such a system is illustrated in FIG. 6. Here, an array of junctions including two electrodes separated by a dielectric layer (see, e.g., FIG. 3) is made, interconnected so that any pair of electrodes addresses just one junction. Each junction can be functionalized with a Cas protein, particular examples being shown as 601 and 603. The protein 601 is addressed via electrodes 610 and 620. The protein 603 is addressed via electrodes 611 and 622. Provided that each junction, or set of junctions (in the case where duplicate measurements are desired), is spaced by an adequate distance (e.g., 10 microns), a different sgRNA can be applied to each junction or set of junctions by spot printing, for example. Thus, the Cas protein 603 may be programmed with one sgRNA 604, while the protein 601 may be programmed with another sgRNA, 602, targeting a different sequence. It will be recognized by one of ordinary skill in the art based on the present disclosure that the connection scheme shown in FIG. 6 may vary and that forming an array of devices is not limited to the particular scheme. For example, each device could be addressed with individual pairs of lead wires.

Example 4

Experiments were also conducted to detect a target sequence from SARS-CoV-2. For these experiments, a guide RNA was used to detect a portion of the nucleocapsid protein of SARS-CoV-2 (see Table 1; SEQ ID NO: 9). Representative data from FIGS. 7A-7B show the distribution of conductance for many dCas9 molecules bound with sgRNA (FIG. 7A), including the distribution measured after target DNA was added. The arrows point to regions of significant changes in conductance (FIG. 7B). Thus, these data demonstrate the efficacy and specificity of the bioelectronic devices of the present disclosure for detecting a viral target nucleic acid.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise. The present disclosure shall control in the event there are any disparities between any definitions and/or description found in the cited references.

What is claimed is:

1. A bioelectronic device for detecting a target nucleic acid comprising:
   a first electrode;
   a second electrode; and
   at least one CRISPR-associated protein comprising a modification to form a chemical bond with the first and the second electrodes, wherein the modification comprises attaching at least two linkers to the CRISPR-associated protein, and wherein at least one of the at least two linkers is attached to each of the first and second electrodes.

2. The device of claim 1, wherein the modification allows an electrical current to pass through the CRISPR-associated protein, and wherein binding of the CRISPR-associated protein to a target nucleic acid causes a shift in the current.

3. The device of claim 1, wherein the CRISPR-associated protein is a Cas family member protein selected from the group consisting of Cas1, Cas2, Cas3, Cas4, Cas5, Cas6, Cas7, Cas8, Cas10, Cas12, Cas13, Cas14, their nuclease-deficient dCas equivalents, and any variants or derivatives thereof.

4. The device of claim 1, wherein the CRISPR-associate protein is Cas9 protein or dCas9.

5. The device of claim 1, wherein the linker is attached to an inactive region of the CRISPR-associated protein via a covalent chemical bond.

6. The device of claim 1, wherein the modification comprises biotinylating the CRISPR-associate protein.

7. The device of claim 1, wherein the linker comprises thio-streptavidin.

8. The device of claim 1, wherein the CRISPR-associate protein and the first and second electrodes are biotinylated, and wherein the linker comprises a streptavidin molecule comprising at least two biotin binding sites.

9. The device of claim 1, wherein the modification comprises a HaloTag fusion protein and a chloroalkane linker.

10. The device of claim 1, wherein the first and/or the second electrode comprises gold, palladium, platinum, silver, copper, or any alloys thereof.

11. The device of claim 1, wherein the first electrode comprises a dielectric layer at least partially covering a top surface of the first electrode.

12. The device of claim 11, wherein the thickness of the dielectric layer is from about 1 nm to about 50 nm.

13. The device of claim 1, wherein the first electrode and second electrode are positioned so that between about a 1 nm and about a 50 nm gap is formed between the two electrodes.

14. The device of claim 13, wherein the gap is from about 2 to about 8 nm.

15. A method of detecting a target nucleic acid using the bioelectronic device of claim 1, the method comprising:
   combining the bioelectronic device and the target nucleic acid with a guide RNA;
   applying a voltage bias between the first and the second electrode that is 100 mV or less; and
   detecting a shift in current upon binding of the CRISPR-associated protein and the guide RNA to the target nucleic acid.

16. The method of claim 15, wherein the guide RNA is complementary to a portion of the target nucleic acid.

17. The method of claim 15, wherein the shift in current comprises a decrease in current as compared to the current when the CRISPR-associated protein is not bound to the target nucleic acid.

18. The method of claim 15, wherein the target nucleic acid is contained in or derived from a sample from a subject.

19. The method of claim 18, wherein the detection of the shift in current indicates that the target nucleic acid is present in the sample.

20. The method of claim 18, wherein the sample is selected from the group consisting of a blood sample, a serum sample, a plasma sample, a saliva sample, a urine sample, a stool sample, and a mucosal sample.

21. The method of claim 15, wherein the target nucleic acid is DNA or RNA.

22. The method of claim 15, wherein the target nucleic acid is derived from or associated with a pathogenic organism.

23. The method of claim 15, wherein the target nucleic acid is derived from or associated with a disease or condition.

24. The method of claim 15, wherein the target nucleic acid is derived from or associated with an engineered organism.

25. The method of claim 22, wherein the target nucleic acid is derived from or associated with a SARS-CoV-2 infection.

26. A system comprising a plurality of the bioelectronic devices of claim 1.

27. The system of claim 26, wherein the plurality of bioelectronic devices are configured to detect more than one target nucleic acid based on corresponding guide RNA sequences.

* * * * *